United States Patent
Park et al.

(10) Patent No.: US 9,562,243 B2
(45) Date of Patent: Feb. 7, 2017

(54) YEAST CELL WITH INACTIVATED OR DEPRESSED PYRUVATE CARBOXYLASE AND METHOD OF PRODUCING LACTATE USING THE YEAST CELL

(71) Applicant: Samsung Electronics Co., Ltd., Suwon-si, Gyeonggi-do (KR)

(72) Inventors: Youngkyoung Park, Seoul (KR); Changduk Kang, Gwacheon-si (KR); Jiyoon Song, Seoul (KR); Juyoung Lee, Daegu (KR); Seunghyun Lee, Asan-si (KR); Kwangmyung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/563,774

(22) Filed: Dec. 8, 2014

(65) Prior Publication Data

US 2015/0159183 A1  Jun. 11, 2015

(30) Foreign Application Priority Data

Dec. 6, 2013  (KR) .................. 10-2013-0151708

(51) Int. Cl.
  *C12P 7/56*  (2006.01)
  *C12N 9/00*  (2006.01)

(52) U.S. Cl.
  CPC . *C12P 7/56* (2013.01); *C12N 9/93* (2013.01); *C12Y 604/01001* (2013.01); *Y02P 20/52* (2015.11)

(58) Field of Classification Search
  None
  See application file for complete search history.

(56) References Cited

U.S. PATENT DOCUMENTS

| 7,368,268 B2 | 5/2008 | Murakami et al. |
| 7,566,563 B2 | 7/2009 | Fatland-Bloom et al. |
| 2007/0031950 A1* | 2/2007 | Winkler .................. C12P 7/56 435/139 |
| 2011/0129885 A1 | 6/2011 | Lang et al. |

FOREIGN PATENT DOCUMENTS

| JP | 2002-535991 A | 10/2002 |
| JP | 2008-067629 B2 | 3/2008 |
| JP | 2011-193788 A | 10/2011 |
| KR | 2008-0069678 A | 7/2008 |

OTHER PUBLICATIONS

Medina et al. Appl and Environ Microbiol, Jan. 2010, vol. 76(1):p. 190-195.*
Mazumdar et al. Appl and Environ Microbiol, Jul. 2010, vol. 76(13):p. 4327-4336.*
Kutyna et al. Microbiological approaches to lowering ethanol concentration in wine, Trends in Food Science & Technology (2010), 21: 293-302.*
Blazeck et al., "Controlling Promoter Strength and Regulation in *Saccharomyces cerevisiae* Using Synthetic Hybrid Promoters", *Biotechnology and Bioengineering*, 109(11): 2884-2895 (2012).
Menendez et al., "Regulatory regions in the promoters of the *Saccharomyces cerevisiae* PYC1 and PYC2 genes encoding isoenzymes of pyruvate carboxylase", *FEMS Microbiology Letters*, 164: 345-352 (1998).
Huet et al., Regulation of pyc1 encoding pyruvate carboxylase isozyme I by nitrogen sources in *Saccharomyces cerevisiae*, *Eur. J. Biochem.*, 267, 6817-6823 (2000).

* cited by examiner

*Primary Examiner* — Iqbal H Chowdhury
(74) *Attorney, Agent, or Firm* — Leydig, Voit & Mayer, Ltd.

(57) ABSTRACT

A yeast cell with reduced pyruvate to oxaloacetate conversion activity, and a method of producing lactate using the yeast cell.

16 Claims, 7 Drawing Sheets

YEAST CELL WITH INACTIVATED OR DEPRESSED PYRUVATE CARBOXYLASE AND METHOD OF PRODUCING LACTATE USING THE YEAST CELL

CROSS-REFERENCE TO RELATED APPLICATIONS

This application claims the benefit of Korean Patent Application No. 10-2013-0151708, filed on Dec. 6, 2013, in the Korean Intellectual Property Office, the disclosure of which is incorporated herein in its entirety by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 91,172 Byte ASCII (Text) file named "716723 ST25.TXT-Revised" created on Feb. 12, 2015.

BACKGROUND

1. Field

The present disclosure relates to a yeast cell with inactivated or depressed pyruvate carboxylase and a method of producing lactate using the yeast cell.

2. Description of the Related Art

Lactate is an organic acid that is broadly used in various industrial fields, such as food, pharmaceutics, chemicals, and electronics. Lactate is colorless, odorless, and a low-volatile material that dissolves well in water. Lactate is non-toxic to the human body and thus may be used as a flavor agent, a taste agent, or a preserving agent. Also, lactate is an environment-friendly alternative polymer material and a raw material of a polylactic acid (PLA) that is biodegradable plastic.

PLA is a polyester-based resin that is produced by ring-open polymerizing a dimer, i.e., lactide, which has been converted from lactic acid and may be variously processed into a film, sheet, fiber, plastic, etc. Thus, demands for PLA as bioplastic have recently increased to broadly replace conventional typical petrochemical plastic, such as polyethylene (PE), polypropylene (PP), polyethylene terephthalate (PET), or polystylene (PS).

In addition, lactate includes both a hydroxyl group and a carboxyl group at the same time and thus is highly reactive. Accordingly, lactate is easily converted into an industrially important compound, such as lactate ester, acetaldehyde, or propyleneglycol, and thus has received attention as an alternative chemical material of the next generation in chemical industry.

Currently, lactate is produced by an industrially petrochemical synthesis process and a biotechnological fermentation process. The petrochemical synthesis process is performed by oxidizing ethylene derived from crude oil, preparing lactonitrile through addition of hydrogen cyanide after acetaldehyde, purifying by distillation, and hydrolyzing by using chloric acid or phosphoric acid. Also, the biotechnological fermentation process is used to manufacture lactate from a reproducible carbon hydrate, such as, starch, sucrose, maltose, glucose, fructose, or xylose, as a substrate.

Therefore, a strain for efficiently producing lactate and a lactate production method using the strain are needed.

SUMMARY

Provided is a genetically engineered yeast cell with an improved ability of producing lactate, wherein the yeast cell has reduced pyruvate to oxaloacetate conversion activity.

Provided is a method of producing lactate by using the yeast cell, and a method of preparing a yeast cell with improved ability to produce lactate.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
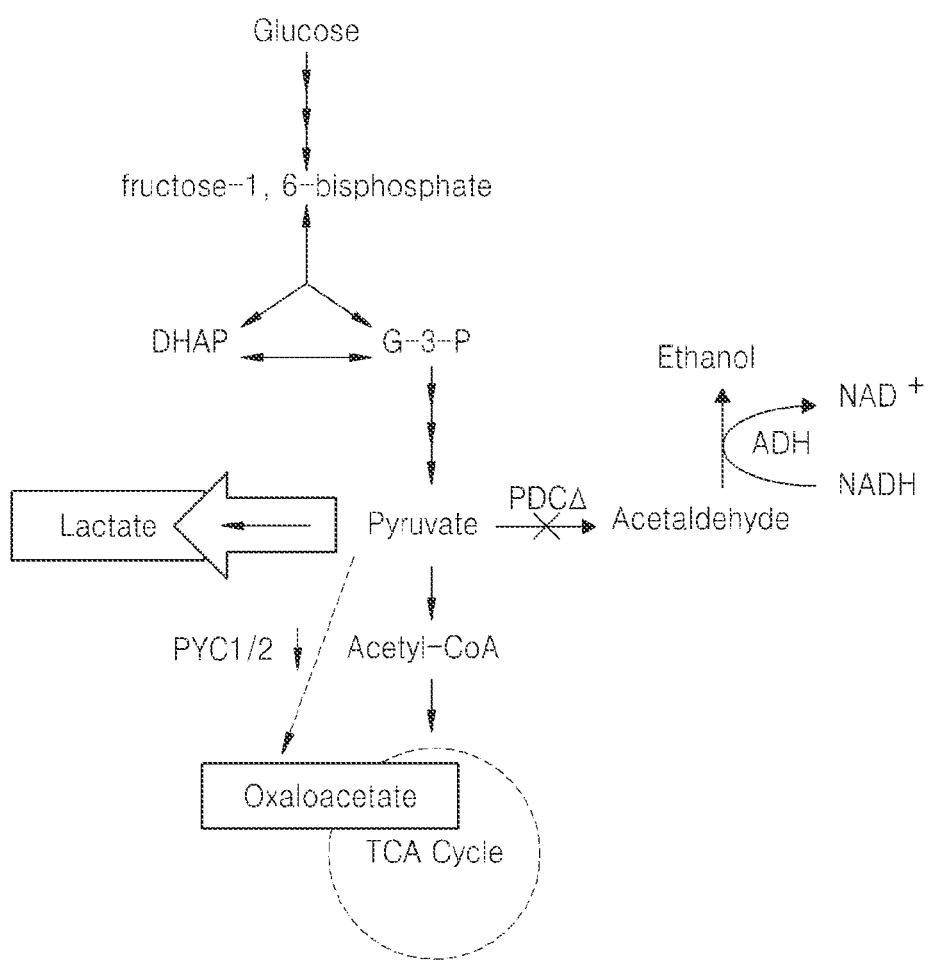
FIG. 1 is a diagram illustrating a lactate production pathway of a yeast cell having an ability of producing lactate.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, provided is a yeast cell comprising an inactivated or reduced ability to convert pyruvate into oxaloacetate. As used herein, the term "lactate" denotes "a lactic acid" or a salt thereof.

As used herein, the term "activity increase", "enzyme activity increase", "increased activity", or "increased enzyme activity" denotes that a cell or an enzyme has an increased activity level compared to an activity level of a comparable cell of the same type or the original enzyme. For example, an enzyme conversion activity from a substrate to a product with respect to a corresponding enzyme may be at least about 5%, at least about 10%, at least about 15%, at least about 20%, at least about 30%, at least about 50%, at least about 60%, at least about 70%, or at least about 100% increased compared to the same biochemical conversion activity of an enzyme produced by a parent cell. A cell having an increased enzyme activity of an enzyme may be confirmed by using any method commonly known in the art.

The term "parent cell" refers to an original cell, for example, a non-engineered cell of the same type as an engineered yeast cell. With respect to a particular genetic modification, the "parent cell" can be a cell that lacks the particular genetic modification, but is identical in all other respects. Thus, a parent cell can be a cell used as starting material to produce a genetically engineered yeast cell having a reduced, inactivated, or depressed activity of a given protein (e.g., a protein having a sequence identity of about 95% or more to a polypeptide that converts pyruvate to oxaloacetate).

Meanwhile, as used herein, an "inactivated" or "depressed" or "reduced" activity of a cell enzyme or a polypeptide, or an enzyme or cell having an activity that is "inactivated" or "depressed" or "reduced" denotes a cell, an isolated enzyme, or a polypeptide having an activity that is lower than an activity measured in a cell of the comparable cell of the same type or the original enzyme, or having no activity. For example, an enzyme conversion activity from a substrate to a product with respect to a corresponding enzyme may be about 20% or more, about 30% or more, about 40% or more, about 50% or more, about 55% or more, about 60% or more, about 70% or more, about 75% or more, about 80% or more, about 85% or more, about 90% or more, about 95% or more, or about 100% reduced than the biochemical conversion activity by an enzyme produced by a parent cell. The cells having reduced activity of the enzyme may be confirmed by using a commonly known method in the art. As used herein, the term "inactivation" may refer to generating a gene that is not expressed at all or a gene encoding a gene product that has no activity even when it is expressed. The term "depression" or "reduction" may refer to generating a gene whose expression level is reduced lower than that of a non-engineered yeast cell, or a gene which encodes a protein with decreased activity although it is expressed.

Also, activity of a cell, polypeptide, or enzyme may be reduced due to deletion or disruption of a gene encoding the polypeptide or enzyme. As used herein, the "deletion" or "disruption" of the gene includes mutation or deletion of the gene or a regulatory region of the gene (e.g., operator, promoter or terminator regions of the gene), or a part thereof, sufficient to disrupt or delete gene function or the expression of a functional gene product. Mutations may include substitutions, insertions, and deletions of one or more bases in the gene or its regulator regions. As a result, the gene is not expressed or has a reduced amount of expression, or the activity of the encoded protein or enzyme is reduced or eliminated. The deletion or disruption of the gene may be accomplished by any suitable genetic engineering technique, such as homologous recombination, mutagenesis, or molecular evolution. When a cell includes a plurality of copies of the same gene or at least two different polypeptide paralogs, at least one gene may be deleted or disrupted.

As used herein, a cell that is not genetically engineered may include a parent cell or a wild-type cell from which a yeast cell comprising an inactivated or reduced ability to convert pyruvate into oxaloacetate is derived by genetic manipulation. The inactivation, depression or reduction of the enzyme may be due to mutation (substitution, addition (insertion) or deletion mutation) of a part of a gene, or deletion of the whole gene. Addition (insertion), substitution, or deletion mutation may be of at least one base group to a gene that encodes the enzyme. The inactivation, depression, reduction may be achieved by gene manipulation such as homogenous recombination, mutation generation, or molecule evolution. When a cell includes a plurality of the same genes or at least two different polypeptide paralogous genes, one or more genes may be inactivated or depressed. The inactivation, depression, reduction may be performed by transforming a vector including some sequences of the gene to a cell, and allowing the sequences to homogeneously recombine with an endogenous gene by culturing the cell, and then by selecting the homogenously recombined cell by using a selection marker.

An activity of the enzyme may be depressed or reduced due to modification of an expression control sequence of a gene, amplification of an expression-decrease related gene, deletion of an expression-increase related gene, or decreased copy number of a gene. The expression control sequence may include an induction promoter, a transcription promotion factor, or a transcription terminator. The modification of an expression control sequence of a gene may include replacing a promoter of a parent cell with a promoter having a low level of expression compared to that of the parent cell. The yeast cell may include a promoter with a low level of expression compared to that of the parent cell.

As used herein, the term "gene" refers to a nucleic acid segment expressing a specific protein, and the gene may or may not include a regulatory sequence of a 5'-non coding sequence and a 3'-non coding sequence.

As used herein, the term "sequence identity" of a nucleic acid or a polypeptide refers to a degree of similarity (i.e. homology) of base groups or amino acid residues between two aligned sequences, when the two sequences are aligned to match each other as possible, at corresponding positions. The sequence identity is a value that is measured by aligning to an optimum state and comparing the two sequences at a particular comparing region, wherein a part of the sequence within the particular comparing region may be added or deleted compared to a reference sequence. A sequence identity percentage may be calculated, for example, by 1) comparing the two sequences aligned within the whole comparing region to an optimum 2) obtaining the number of matched locations by determining the number of locations represented by the same amino acids of nucleic acids in both of the sequences, 3) dividing the number of the matched locations by the total number of the locations within the comparing region (i.e., a range size), and 4) obtaining a percentage of the sequence identity by multiplying 100 to the result. The sequence identity percent may be determined by using a common sequence comparing program, for example, BLASTN or BLASTP (NCBI), CLC Main Workbench (CLC bio), or MegAlign™ (DNASTAR Inc).

In confirming many different polypeptides or polynucleotides having the same or similar function or activity, sequence identities at several levels may be used. For example, the sequence identities may be about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, about 99% or greater, or 100%.

The yeast cell may have an improved ability of producing lactate. The yeast cell with an improved lactate productivity refers to a yeast cell with an increased lactate productivity compared to that of a parent cell.

Also, the yeast cell may be ascomycota. The ascomycota may be saccharomycetacease. The saccharomycetaceae may be *Saccharomyces* genus, *Kluyveromyces* genus, *Candida* genus, *Pichia* genus, *Issatchenkia* genus, *Debaryomyces* genus, *Zygosaccharomyces* genus, *Shizosaccharomyces* genus, or *Saccharomycopsis* genus. The *Saccharomyces* genus may be, for example, *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum,* or *S. zonatus*. The *Kluyveromyces* genus may be *Kluyveromyces lactis, Kluyveromyces marxianus,* or *Kluyveromyces thermotolerans*. The *Candida* genus may be *Candida glabrata, Candida boidinii, Candida magnolia, Candida methanosorbosa, Candida sonorensis,* or *Candida utilis*. The *Pichia* genus may be *Pichia stipitis*. The *Issatchenkia* genus may be *Issatchenkia orientalis*. The *Debaryomyces* genus may be *Debaryomyces hansenii*. The *Zygosaccharomyces* genus may be *Zygosaccharomyces bailli* or *Zygosaccharomyces rouxii*. The *Shizosaccharomyces* genus may be *S. cryophilus, S. japonicus, S. octosporus,* or *S. pombe*.

Also, the enzyme cell may include a mutant enzyme cell for producing a desired produce, such as lactate, as well as a natural enzyme cell. The mutant enzyme cell may have resistance with respect to, for example, uracil, sulfurguanidine, sulfathiazole, azaserine, trimethoprim, or monofluoroacetate.

The polypeptide capable of converting pyruvate to oxalate may catalyze reactions, such as magnesium-ATP dependent carboxylation from pyruvate to oxaloacetate and biotin-dependent carboxylation. The polypeptide may convert pyruvate into oxaloacetate when one ATP is consumed. The polypeptide may be an enzyme that is classified as EC 6.4.1.1. The polypeptide may be two pyruvate carboxylase isoenzymes (PYC1 and PYC2) among enzymes of *Saccharomyces* genus. The polypeptide capable of converting pyruvate to oxaloacetate may have an amino acid sequence having about 50% or more, about 70% or more, about 80% or more, about 90% or more, about 95% or more, about 96% or more, about 97% or more, about 98% or more, about 99% or more, or about 100% or more of a sequence identity with an amino acid sequence of SEQ ID NO: 1 (GenBank ID: NP_011453.1) and/or SEQ ID NO: 2 (GenBank ID: NP_009777.1). The two pyruvate carboxylase isoenzymes may be encoded by different genes. Each of the genes may have a nucleotide sequence of SEQ ID NO: 3 (GI Number: 6321376) and/or SEQ ID NO: 4 (GI Number: 63196950). The gene may be PYC1 or PYC2 that encodes a pyruvate carboxylase (PYC). The modification of an expression control sequence of a gene of PYC1, PYC2, or a combination thereof may be performed by replacing promoters $P_{PYC1}$ and $P_{PYC2}$ of a parent cell with promoters having a lower expression level than those of the parent cell. The promoters may be operably connected to the coding region of the polypeptide converting pyruvate to oxalate. The promoters having a low expression level may be, for example, a LEUM promoter ($P_{leum}$), a cyc1 promoter ($P_{cyc1}$), or a mutant thereof. Also, the promoters having a lower expression level than those of the promoters of a parent cell, $P_{PYC1}$ and $P_{PYC2}$, may be, for example, TEF1, a GPC promoter, or a GAL promoter.

In the yeast cell, an activity of a polypeptide capable of converting pyuruvate to acetaldehyde, a polypeptide capable of converting lactate to pyruvate, a polypeptide capable of converting dehydroxyacetone phosphate (DHAP) to glycerol-3-phosphate, an external mitochondrial NADH dehydrogenase, or a combination may be inactivated or depressed. The yeast cell may comprise a deletion or disruption mutation of a gene encoding a polypeptide that converts pyruvate to acetaldehyde, a gene encoding a polypeptide that converts lactate to pyruvate, a gene encoding a polypeptide that converts dehydroxyacetone phosphate (DHAP) to glycerol-3-phosphate, a gene encoding an external mitochondria NADH dehydrogenase, or a combination thereof.

In the yeast cell, an activity of a polypeptide capable of converting pyruvate to acetaldehyde may be inactivated or depressed. The polypeptide converting pyruvate to acetaldehyde may belong to EC 4.1.1.1. The polypeptide capable of converting pyruvate to acetaldehyde may have an amino acid sequence having about 50% or more, about 70% or more, about 80% or more, about 90% or more, about 95% or more, about 96% or more, about 97% or more, about 98% or more, about 99% or more, or about 100% or more of a sequence identity with an amino acid sequence of SEQ ID NO: 5. A gene that encodes the polypeptide capable of converting pyruvate to acetaldehyde may be pdc1 or pdc2 that encodes a pyruvate decarboxylase (PDC). For example, the gene that encodes the polypeptide capable of converting pyruvate to acetaldehyde may have a nucleotide sequence of SEQ ID NO: 6. The activity of the polypeptide may be reduced due to a mutation (addition, substitution, or deletion or one or more bases) in the gene, or deletion of all or part of the gene. For example, the activity of the polypeptide may be reduced due to a deletion or disruption mutation of a gene encoding a polypeptide that converts pyruvate to acetaldehyde.

The yeast cell may have an inactivated or depressed activity of a polypeptide capable of converting lactate to pyruvate. The polypeptide capable of converting lactate to pyruvate may be a cytochrome c-dependent enzyme. The polypeptide capable of converting lactate to pyruvate may be a lactate cytochrome-c oxydoreductase (CYB2). The lactate cytochrome c-oxydoreductase may be an enzyme that is classified as EC 1.1.2.4 acting on D-lactate or EC 1.1.2.3 acting on L-lactate. The polypeptide capable of converting lactate to pyruvate may include an amino acid sequence having about 50% or more, about 70% or more, about 80% or more, about 90% or more, about 95% or more, about 96% or more, about 97% or more, about 98% or more, about 99% or more, or about 100% or more sequence identity with an amino acid sequence of SEQ ID NO: 7. The gene that encodes the polypeptide capable of converting lactate to pyruvate may have a nucleotide sequence of SEQ ID NO: 8. The activity of the polypeptide may be reduced due to a mutation (addition, substitution, or deletion or one or more bases) in the gene, or deletion of all or part of the gene. For example, the activity of the polypeptide may be reduced due to a deletion or disruption mutation of a gene encoding a polypeptide that converts lactate to pyruvate.

In the yeast cell, the activity of a polypeptide capable of converting DHAP to glycerol-3-phosphate may be inactivated or depressed. The polypeptide capable of converting DHAP to glycerol-phosphate may be an enzyme catalyzing reduction of DHAP to glycerol-3-phosphate by using oxidation of NAD(P)H to NAD(P)$^+$. The enzyme may belong to EC 1.1.1.8. The polypeptide may be cytosolic glycerol-3-phosphate dehydrogenase (GPD1). The polypeptide capable of converting DHAP to glycerol-3-phosphate may include an amino acid sequence having about 50% or more, about 70% or more, about 80% or more, about 90% or more, about 95% or more, about 96% or more, about 97% or more, about 98% or more, about 99% or more, or about 100% or more sequence identity with an amino acid sequence SEQ ID NO: 9. The gene that encodes the polypeptide capable of converting DHAP to glycerol-3-phosphate may have a nucleotide sequence of SEQ ID NO: 10. The gene may be GPD1 that encodes a glycerol-3-phosphate dehydrogenase. The activity of the polypeptide may be reduced due to a mutation (addition, substitution, or deletion or one or more bases) in the gene, or deletion of all or part of the gene. For example, the activity of the polypeptide may be reduced due to a deletion or disruption mutation of a gene encoding a polypeptide that converts dehydroxyacetone phosphate (DHAP) to glycerol-3-phosphate.

In the yeast cell, an activity of the external mitochondrial NADH dehydrogenase may be inactivated or depressed. The external mitochondrial NADH dehydrogenase may be an enzyme that is classified as EC. 1.6.5.9 or EC. 1.6.5.3. The NADH dehydrogenase may be type II NADH:ubiquinone oxidoreductase. The NADH dehydrogenase may be located on an outer surface of an inner mitochondrial membrane facing the cytoplasm. The NADH dehydrogenase may be an enzyme that catalyzes oxidation of cytosolic NADH to NAD$^+$. The NADH dehydrogenase may re-oxidize the cytosolic NADH formed therefrom. The NADH dehydrogenase may provide the cytosolic NADH to a mitochondrial respiratory chain. The NADH dehydrogenase may be NDE1, NDE2, or a combination thereof. The NADH dehydrogenase may be different from an internal mitochondrial NADH dehydrogenase, NDI1, that is located and functions inside the mitochondria. The NDE1 and NDE2 may each have an amino acid sequence having about 50% or more, about 70% or more, about 80% or more, about 90% or more, about 95% or more, about 96% or more, about 97% or more, about 98% or more, about 99% or more, or about 100% or more sequence identity with an amino acid sequence SEQ ID NO: 11 or 12. A gene encoding NDE1 and a gene encoding NDE2 may each have a nucleotide sequence of SEQ ID NO: 13 or 14. The activity of the polypeptide may be reduced due to a mutation (addition, substitution, or deletion or one or more bases) in the gene, or deletion of all or part of the gene. For example, the activity of the polypeptide may be reduced due to a deletion or disruption mutation of a gene encoding an external mitochondria NADH dehydrogenase.

In the yeast cell, an activity of the polypeptide capable of converting pyruvate to lactate may increase. In the yeast cell, the lactate dehydrogenase activity converting pyruvate to lactate may be increased due to an increased expression of lactate dehydrogenase converting pyruvate to lactate.

The increased LDH expression may be caused by introduction of a gene encoding a lactate dehydrogenase. The gene may be an exogenous gene. The exogenous gene may be homologous or heterologous. The exogenous gene that encodes a lactate dehydrogenase may be introduced at a downstream position of a promoter enabling expression of a gene that encodes a lactate dehydrogenase. Also, a polynucleotide that encodes a lactate dehydrogenase (also, referred to as "LDH") may be included in a genome of a yeast cell. When a polynucleotide encoding LDH functions for production of active proteins in a cell, the polynucleotide is considered "functional" in a cell. A yeast cell including the polynucleotide encoding L-LDH or D-LDH may produce a L-lactate enantiomer, a D-lactate enantiomer, or a salt thereof.

The copy number of the gene encoding LDH may increase due to the introduced gene that encodes LDH.

The yeast cell may include a gene that encodes one lactate dehydrogenase or multiple genes that encode 1 to 10 copies of lactate dehydrogenase. The multiple genes may encode, for example, 1 to 8, 1 to 5, 1 to 4, or 1 to 3 copies of lactate dehydrogenase. When the yeast cell includes the genes encoding multiple copies of lactate dehydrogenase, each of the genes may be a copy of the same gene or may include a copy of a gene that encodes at least two different lactate dehydrogenases. Multiple copies of a gene encoding exogenous lactate dehydrogenase may be included in the same locus or in multiple loci within a host cell's genome. The exogenous lactate dehydrogenase may have a better activity than an endogenous lactate dehydrogenase of a yeast cell.

The gene encoding lactate dehydrogenase may be derived from bacteria, yeast, fungi, mammals, or reptiles. The gene may be a polynucleotide that encodes at least one lactate dehydrogenase selected from *Pelodiscus sinensis japonicus*, *Ornithorhynchus anatinus*, *Tursiops truncatus*, *Rattus norvegicus*, and *Xenopus laevis*. A lactate dehydrogenase derived from *Pelodiscus sinensis japonicas*, a lactate dehydrogenase derived from *Ornithorhynchus anatinus*, a lactate dehydrogenase derived from *Tursiops truncatus*, a lactate dehydrogenase derived from *Rattus norvegicus*, and a lactate dehydrogenase derived from *Xenopus laevis* may, each respectively, have amino acid sequences having about 50% or more, 60% or more, 70% or more, 80% or more, 90% or more, 95% or more, 96% or more, 97% or more, 98% or more, 99% or more, or 100% of sequence identity with amino acid sequences of SEQ ID NO: 15, 16, 17, and 18. A gene that encodes the lactate dehydrogenase may have a nucleotide sequence of SEQ ID NO: 19.

The polynucleotide encoding lactate dehydrogenase may be expressed from a vector including lactate dehydrogenase derived from bacteria, yeast, fungus, mammals, or reptiles. The vector may include a replication origin, a promoter, a polynucleotide encoding a lactate dehydrogenase, and a terminator. The replication origin may include a yeast autonomous replication sequence (ARS). The yeast ARS may be stabilized by a yeast centrometric sequence (CEN). The promoter may be selected from the group consisting of a CYC promoter, a TEF promoter, a GPD promoter, and an ADH promoter. The CYC promoter, TEF promoter, GPD promoter, ADH promoter, and CCW12 promoter may have, each respectively, nucleotide sequences of SEQ ID NO: 21, 22, 23, 24, and 73. The terminator may be selected from the group consisting of phosphoglycerate kinase 1 (PGK1), cytochrome c transcription (CYC1), and GAL1. The CYC1 terminator may have a nucleotide sequence of SEQ ID NO: 25. The vector may further include a selection marker.

In the yeast cell, an activity of a polypeptide capable of converting pyruvate to oxaloacetate is depressed. The depression of the activity of a polypeptide may be caused by replacement of an expression control sequence of a gene encoding the polypeptide with a promoter having a low level of expression compared to that of the parent cell, an inactivated or depressed activity of a gene that encodes the polypeptide capable of converting pyruvate to acetaldehyde, a gene that encodes the polypeptide capable of converting lactate to pyruvate, a gene that encodes the polypeptide capable of converting DHAP to glycerol-3-phosphate, a gene that converts the polypeptide capable of converting external mitochondrial NADH dehydrogenase, or a combination, or introduction of a gene that encodes the polypeptide capable of converting pyruvate to lactate into the yeast cell. The polypeptide capable of converting pyruvate to oxaloacetate may be a pyruvate carboxylase 1 (PYC1), a pyruvate carboxylase 2 (PYC2), or a combination thereof.

In the yeast cell, an activity of the polypeptide capable of converting pyruvate to oxaloacetate is inactivated or depressed. The depression of an activity of PYC2, which is one of polypeptides converting pyruvate to oxaloacetate, may be caused by replacement of an expression control sequence of a gene encoding the polypeptide with a promoter having a low level of expression compared to that of the parent cell. The inactivation of the activity of PYC2 may be caused by substitution, addition, or deletion of a part of or the whole gene encoding the polypeptide, an inactivated or depressed activity of a gene that encodes the polypeptide capable of converting pyruvate to acetaldehyde, a gene that encodes the polypeptide capable of converting lactate to pyruvate, a gene that encodes the polypeptide capable of converting DHAP to glycerol-3-phosphate, a gene that converts the polypeptide capable of converting external mitochondrial NADH dehydrogenase, or a combination, or introduction of a gene that encodes the polypeptide capable of converting pyruvate to lactate into the yeast cell.

The yeast cell may produce lactate at a yield that is about 4.5 to about 15%, about 5 to about 15%, about 6 to about 15%, about 7.5 to about 15%, about 8 to about 15%, about 8 to about 14%, or about 8 to about 13.8% or more increased than that of the parent cell, in which an activity of the polypeptide capable of converting pyruvate to oxaloacetate is not inactivated or depressed. Also, the yeast cell may produce lactate at a yield of about 45.5 to about 51% or more, or about 45.5% to about 50.5%, which is a ratio of an amount of consumed glucose to an amount of produced lactate.

According to another embodiment of the present invention, provided is a method of preparing lacate, wherein the method includes culturing the yeast cell described above in a cell culture medium, whereby the yeast cell produces lactate, and collecting lactate from the culture.

The culturing may be performed in a carbon source, for example, a medium containing glucose. The medium used in the culturing of a yeast cell may be a common medium suitable for growth of a host cell such as a minimal or composite medium containing appropriate supplements.

The medium used in the culturing may be a medium that satisfies particular conditions for growing a yeast cell. The medium may be one selected from the group consisting of a carbon source, a nitrogen source, a salt, trace elements, and a combination thereof.

The culturing condition for obtaining lactate from the genetically engineered yeast cell may be appropriately controlled. The culturing may be performed in an aerobic or anaerobic condition. For example, the yeast cell is cultured under an aerobic condition for its proliferation, and then, the yeast cell is cultured under an anaerobic condition to produce lactate. The anaerobic condition may include a dissolved oxygen (DO) concentration of 0% to 10%, for example, 0% to 8%, 0% to 6%, 0% to 4%, or 0% to 2%. A pH of a fermented solution may be controlled to be maintained in a range of about 2 to about 7.

The culturing of the yeast cell may be a continuous type, a semi-continuous type, a batch type, or a combination thereof.

The term "culture condition" indicates a condition for culturing a yeast cell. Such culture condition may be, for example, a carbon source, a nitrogen source, or an oxygen condition for the yeast cell to use. The carbon source used by the yeast cell includes monosaccharides, disaccharides, or polysaccharides. In particular, the carbon source may be glucose, fructose, mannose, or galactose. The nitrogen source used by the yeast cell may include an organic nitrogen compound or an inorganic nitrogen compound. In particular, the nitrogen source may be an amino acid, amide, amine, a nitrate, or an ammonium salt. The oxygen condition for culturing the yeast cell includes an aerobic condition of a normal oxygen partial pressure, a low-oxygen condition including 0.1% to 10% of oxygen in the atmosphere, or an anaerobic condition without oxygen. A metabolic pathway may be modified in accordance with the carbon source or the nitrogen source that may be practically used by the yeast cell.

Obtaining the lactate from the culture may be performed by separating the lactate from the culture by using a method commonly known in the art. The separation method may be centrifuge, filtration, ion-exchange chromatography, or crystallization. For example, the culture may be centrifuged at a low rate to remove a biomass, and the supernatant resulting therefrom may be separated through ion-exchange chromatography.

The present invention will be described in further detail with reference to the following examples. These examples are for illustrative purposes only and are not intended to limit the scope of the present invention.

Example 1

Preparation of Strain for Highly-Efficient Production of Lactate and Preparation of Expression Vector In order to block a production pathway of ethanol and glycerol as main byproducts, a pyruvate decarboxylase (pdc1) gene, which is a main enzyme of alcohol fermentation, a NAD-dependent glycerol-3-phosphate dehydrogenase (GPD1) gene, which is a main enzyme of glycerol biosynthesis, and a L-lactate cytochrome-c oxidoreductase2 (cyb2) gene, which is a lactate lyase, were inactivated by homogenous recombination using *Saccharomyces cerevisiae* CEN.PK2-1D (MATα ura3-52; trp1-289; leu2-3, 112; his3Δ1; MAL2-8$^C$; SUC2, EUROSCARF accession number: 30000B) as a lactate production strain.

(1.1) Preparation of L-LDH Overexpression Vector and Inactivated Vectors of pdc1, GPD1, and cyb2 Genes (1.1.1) Preparation of a L-LDH Overexpression Vector A CCW12 promoter PCR fragment obtained by performing PCR with a genomic DNA of *Saccharomyces cerevisiae* CEN.PK2-1D as a template and using primers of SEQ ID NO: 26 and SEQ ID NO: 27 was digested with SacI and XbaI, and the resultant was inserted into p416-GPD vector (ATCC 87360™) digested with SacI and XbaI, producing p416-CCW12p vector.

Then, L-ldh gene (SEQ ID NO: 19) was amplified from *Pelodiscus sinensis japonicus* genomic DNA by PCR using primers of SEQ ID NO: 28 and SEQ ID NO: 29. The resulting L-ldh PCR fragment and p416-CCW12p obtained therefrom were digested with BamHI and SalI, and ligated, producing p416-CCW12p-LDH, which is an L-ldh expression vector.

The L-ldh expression vector has also a yeast autonomous replication sequence (ARS)/a yeast centrometric sequence (CEN) of SEQ ID NO: 20, a CYC promoter of SEQ ID NO: 21, a CCW12 promoter of SEQ ID NO: 73, and a CYC1 terminator of SEQ ID NO: 25. The L-ldh expression vector included a polynucleotide encoding L-ldh derived from *Pelodiscus sinensis japonicus* of SEQ ID NO: 19.

Figure 2:
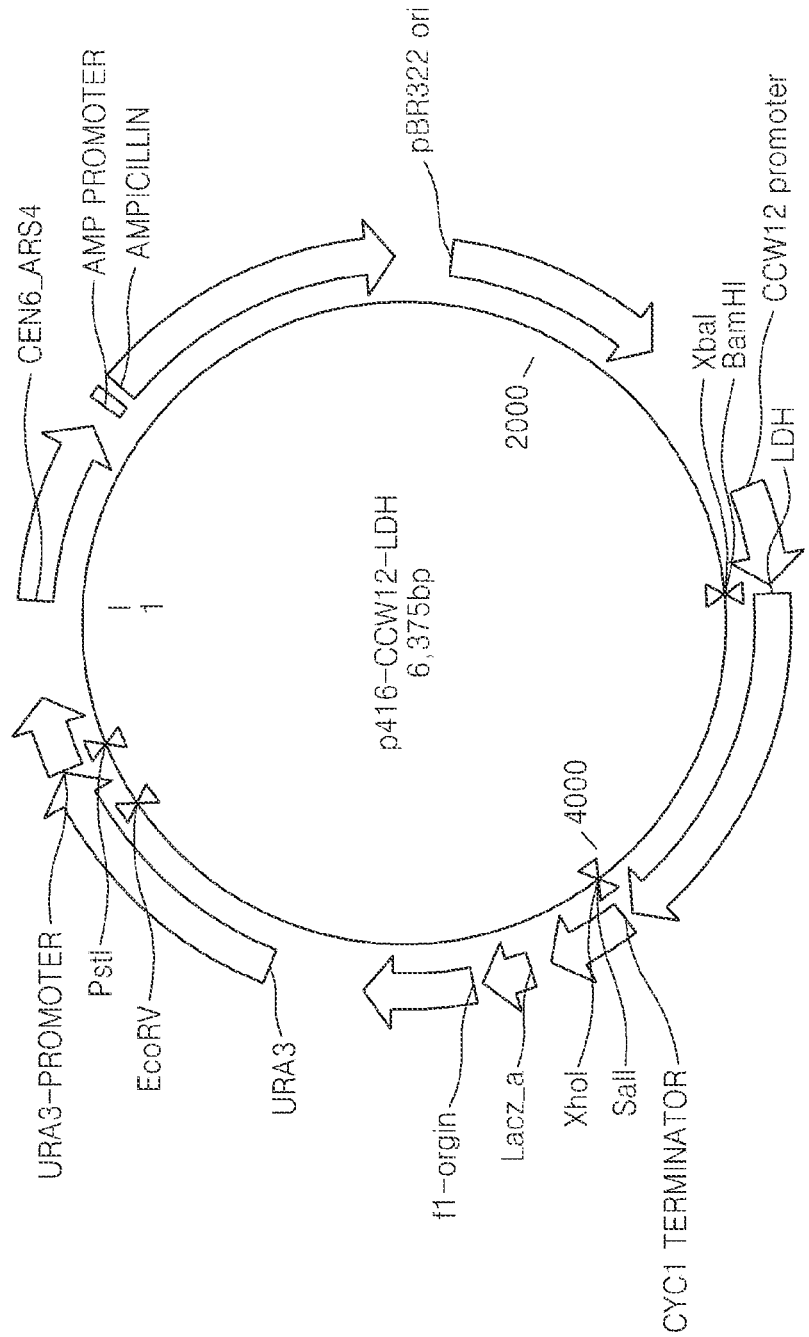
FIG. 2 is a diagram illustrating a p416-CCW12p-LDH vector.

FIG. 2 is a view illustrating a p416-CCW12p-LDH vector. As shown in FIG. 2, the LDH derived from *Pelodiscus sinensis japonicus* was introduced into the vector.

(1.1.2) Preparation of a Gene Exchange Vector

Figure 3:
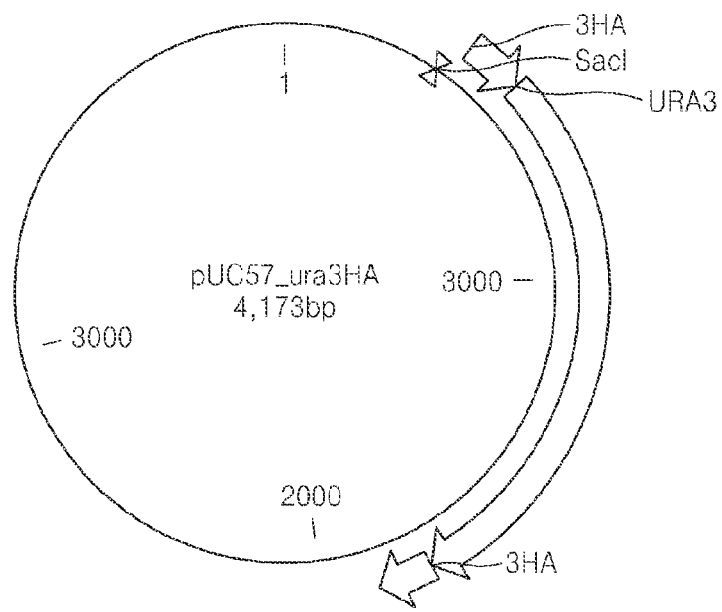
FIG. 3 is a diagram illustrating a pUC57-ura3HA vector.
Figure 4:
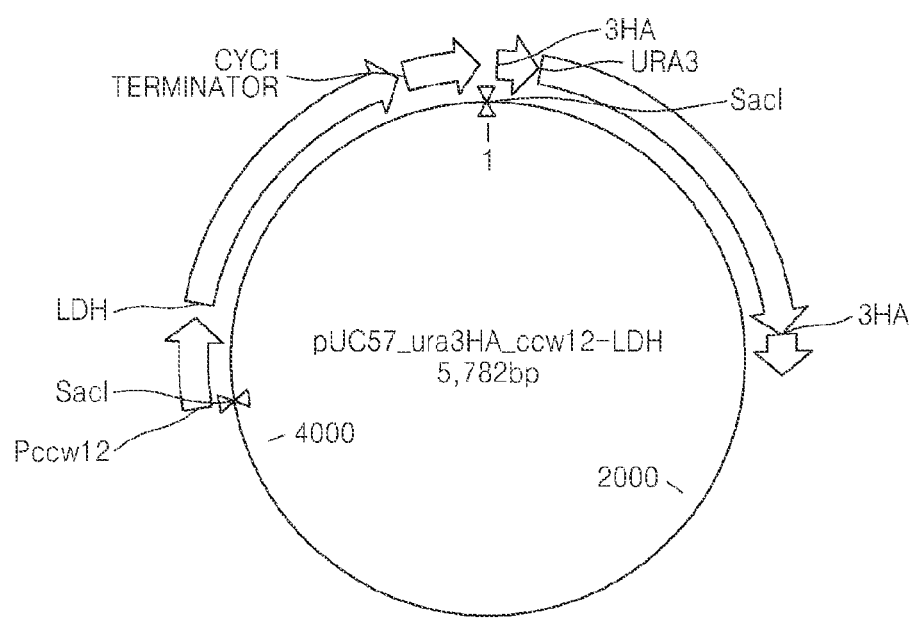
FIG. 4 is a diagram illustrating a pUC57-CCW12p-LDH-ura3HA vector.

PDC1, CYB2, and GPD1 genes were deleted by using a homologous recombination method, and at the same time, a gene exchange vector for introducing an L-LDH gene was prepared in the same manner described below. FIG. 2 illustrates a pUC57-ura3HA (Genetics 116: 541-545, August, 1987) vector. FIG. 3 illustrates a pUC57-CCW12p-LDH-ura3HA vector.

PCR was performed using the prepared p416-CCW12p-LDH as a template with primers of SEQ ID NOS: 30 and 31. The resulting PCR fragment and the prepared pUC57-ura3HA vector were digested with SacI and ligated, producing pUC57-CCW12p-LDH-ura3HA.

PCR was performed using the produced pUC57-CCW12p-LDH-ura3HA as a template with primers of SEQ ID NOS: 32 and 33, producing a pdc1 gene deletion cassette.

PCR was performed using the produced pUC57-CCW12p-LDH-ura3HA as a template with primers of SEQ ID NOS: 34 and 35, producing a cyb2 gene deletion cassette.

PCR was performed using the produced pUC57-CCW12p-LDH-ura3HA as a template with primers of SEQ ID NOS: 36 and 37, producing a GPD1 gene deletion cassette.

(1.2) Inactivation of pdc1, GPD1, and cyb2 Genes

A mutant strain of *Saccharomyces cerevisiae* CEN.PK2-1D, in which pdc1 is deleted, was produced in the same manner as follows. *Saccharomyces cerevisiae* CEN.PK2-1D was plated onto a YPD agar plate (including 10 g of yeast extract, 20 g of peptone, and 20 g of glucose) and incubated for 24 hours at 30° C., and then, a colony obtained therefrom was inoculated in about 10 ml of a YPD liquid medium and cultured for about 18 hours at about 30° C. The sufficiently grown culture solution was inoculated in about 50 ml of a YPD liquid medium contained in a 250 ml-flask at a concentration of 1% (v/v) and cultured in an incubator at a rate of about 230 rpm and at 30° C. After about 4 to 5 hours, when the $OD_{600}$ reached about 0.5, the culture was centrifuged at a rate of about 4,500 rpm for about 10 minutes to harvest cells, and the cells were resuspended in a lithium acetate solution at a concentration of about 100 mM. Then, the cells were harvested by performing centrifugation at a rate of about 4,500 rpm for about 10 minutes, resuspended in a lithium acetate solution at a concentration of about 1 M, and then divided into a volume of about 100 µl each.

In order to delete a pdc1 gene, the PDC1 deletion cassette produced in Example 1.1.2 was mixed with 50% of polyethyleneglycol and a single stranded carrier DNA and reacted in a water tub for about 1 hour at 42° C., and then, the culture solution was spread on a uracil-free minimal agar plate (including YSD, 6.7 g/L of yeast nitrogen base without amino acids, and 1.4 g/L of amino acid dropout mix (-ura)) and grown for about 24 hours or more at 30° C. Ten colonies (mutant strains) grown on the plate were selected, patched onto the fresh uracil-free minimal agar plate, and at the same time, inoculated into a liquid medium including the same components contained in the uracil-free minimal agar plate to isolate the genomic DNA from the above mutant strains by using a commonly used kit (Gentra Puregene Cell kit, Qiagen, USA). In order to confirm deletion of pdc1 gene, PCR was performed using the isolated genomic DNA of the mutant strain as a template with primers of SEQ ID NOS: 38 and 39, and then, electrophoresis was performed on the obtained PCR product to confirm pdc1 deletion. As a result, *Saccharomyces cerevisiae* CEN.PK2-1D (Δpdc1::ldh+ura3) was obtained.

Also, for additional gene deletion using the gene exchange vector, a selection marker URA3 gene, which was introduced for the preparation of a CEN.PK2-1D (Δpdc1::ldh+ura3) strain, was removed from those strain. *Saccharomyces cerevisiae* CEN.PK2-1D (Δpdc1::ldh+ura3) was inoculated in about 10 ml of a YPD liquid medium, cultured for about 18 hours at 30° C., and spread on a 5-FOA plate (including YSD, 6.7 g/L of yeast nitrogen base without amino acids, 1.4 g/L of an amino acid dropout mix, and 1 µg/L of 5-fluoroorotic acid), and cultured for about 24 hours or more at 30° C. Ten colonies (a URA3 pop-out strain) grown on the 5-FOA plate were selected, patched onto the fresh 5-FOA plate, and, at the same time, cultured in a YPD liquid medium to isolate genomic DNA from the selected strain by using a commonly used kit (Gentra Puregene Cell kit, Qiagen, USA). In order to confirm deletion of URA3 gene by using the isolated genomic DNA of the URA3 pop-out strain as a template, PCR was performed using primers of SEQ ID NOS: 38 and 39, and then electrophoresis was performed on the obtained PCR product to confirm deletion of URA3 gene. As a result, *Saccharomyces cerevisiae* CEN.PK2-1D (Δpdc1::ldh) was obtained.

A mutant strain of *Saccharomyces cerevisiae* CEN.PK2-1D (Δpdc1::ldh), in which cyb2 gene is deleted, was prepared in the same manner as used in the deletion of the pdc1 gene.

In order to delete a cyb2 gene, the cyb2 deletion cassette prepared in Example 1.1.2 was introduced to the *Saccharomyces cerevisiae* CEN.PK2-1D (Δpdc1::ldh), which was resuspended in a lithium acetate solution, in the same manner as used in the deletion of the pdc1 gene, ten colonies grown on a plate were selected to isolate a genomic DNA. In order to confirm deletion of cyb2, PCR was performed by having the isolated genomic DNA as a template and primers of SEQ ID NOS: 40 and 41, and then electrophoresis was performed on the obtained PCR product to confirm deletion of cyb2 gene. As a result, *Saccharomyces cerevisiae* CEN.PK2-1D (Δpdc1::ldhΔcyb2::ldh+ura3) was obtained.

Also, for additional gene deletion using the gene deletion vector, a selection marker URA3 gene was removed from *Saccharomyces cerevisiae* CEN.PK2-1D (Δpdc1::ldhΔcyb2::ldh+ura3) in the same manner used in the URA3 pop-out method as described above. Ten colonies grown on a plate were selected to isolate a genomic DNA. In order to confirm deletion of URA3 gene by using the isolated genomic DNA of the URA3 pop-out strain as a template, PCR was performed using primers of SEQ ID NOS: 40 and 41, and then electrophoresis was performed on the obtained PCR product to confirm deletion of URA3 gene. As a result, *Saccharomyces cerevisiae* CEN.PK2-1D (Δpdc1::ldhΔcyb2::ldh) was obtained.

A mutant strain of *Saccharomyces cerevisiae* CEN.PK2-1D (Δpdc1::ldhΔcyb2::ldh), in which GPD1 gene is deleted, was prepared in the same manner as used in the deletion of the pdc1 gene.

In order to delete a GPD1 gene, the GPD1 deletion cassette prepared in Example 1.1.2 was introduced to the *Saccharomyces cerevisiae* CEN.PK2-1D (Δpdc1::ldhΔcyb2::ldh), which was resuspended in a lithium acetate solution, in the same manner as used in the deletion of the pdc1 gene and the deletion of the cyb2 gene, ten colonies grown on a plate were selected to isolate a genomic DNA. In order to confirm deletion of GPD1, PCR was performed by having the isolated genomic DNA as a template and primers of SEQ ID NOS: 42 and 43, and then electrophoresis was performed on the obtained PCR product to confirm deletion of GPD1 gene. As a result, *Saccharomyces cerevisiae* CEN.PK2-1D (Δpdc1::ldhΔcyb2::ldhΔGPD1::ldh+ura3) was obtained.

Also, for additional gene deletion using the gene deletion vector, a selection marker URA3 gene was removed from *Saccharomyces cerevisiae* CEN.PK2-1D (Δpdc1::ldhΔcyb2::ldhΔgpd1::ldh+ura3) in the same manner used in the URA3 pop-out method as described above. Ten colonies grown on a plate were selected to isolate a genomic DNA. In order to confirm deletion of URA3 gene by using the isolated genomic DNA of the URA3 pop-out strain as a template, PCR was performed using primers of SEQ ID NOS: 42 and 43, and then electrophoresis was performed on the obtained PCR product to confirm deletion of URA3 gene. As a result, *Saccharomyces cerevisiae* CEN.PK2-1D (Δpdc1::ldhΔcyb2::ldhΔgpd1::ldh) was obtained.

*Saccharomyces cerevisiae* CEN.PK2-1D (Δpdc1::ldhΔcyb2::ldhΔgpd1::ldh) was deposited in Korean Collection for Type Cultures (KCTC) on May 30, 2013, and received an accession number KCTC 12415BP.

(1.3) LDH Enhancement

L-ldh may be additionally introduced to a genome to KCTC12415BP to additionally control and to enhance the lactate production pathway for increasing lactate production, such as redox balance enhancement or glycolysis pathway engineering, and the method is described below.

(1.3.1) Preparation of Vector with L-ldh Introduced into Genome

Figure 5:
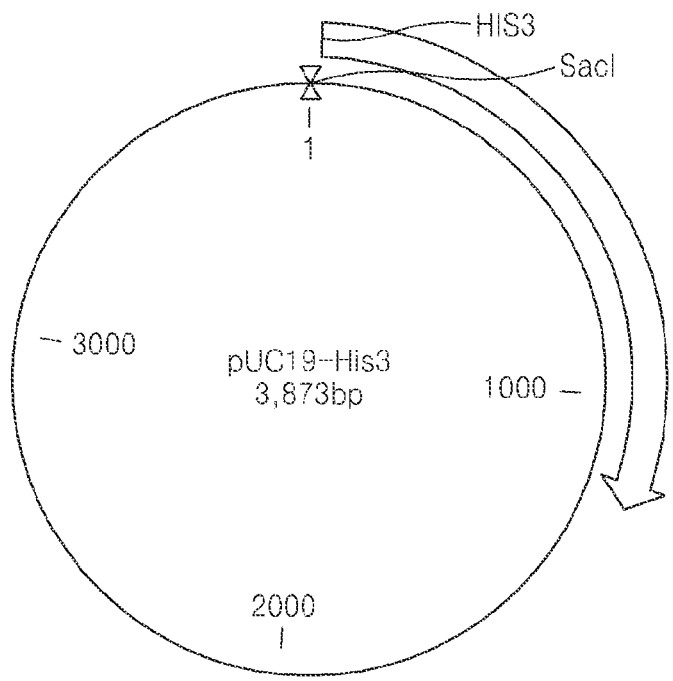
FIG. 5 is a diagram illustrating a pUC19-HIS3 vector.
Figure 6:
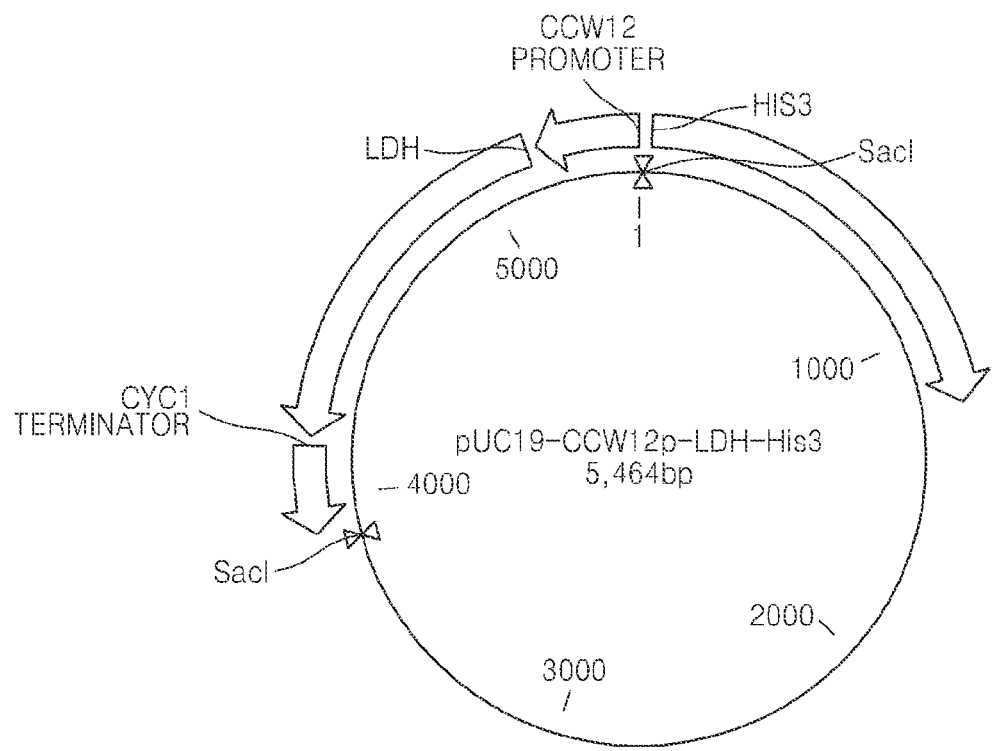
FIG. 6 is a diagram illustrating a pUC19-CCW12p-LDH-His3 vector.

For additional introduction of L-ldh, a gene introduction vector was prepared as follows. FIG. 5 illustrates a pUC19-HIS3 vector (Appl Environ Microbiol. 2002 May; 68(5): 2095-100), which may use a HIS3 gene as a selection marker. FIG. 6 illustrates a pUC19-CCW12p-LDH-HIS3 vector.

PCR was performed using the prepared p416-CCW12p-LDH as a template and primers of SEQ ID NO: 30 and SEQ ID NO: 31. The resulting PCR fragment and the pUC19-HIS3 vector obtained therefrom were digested with SacI, and ligated, producing pUC19-CCW12p-LDH-HIS3.

Also, for additional introduction of L-ldh into a genome of a KCTC12415BP strain, PCR was performed using the prepared pUC19-CCW12p-LDH-HIS3 as a template and primers of SEQ ID NO: 34 and SEQ ID NO: 45, thereby preparing a cassette to be inserted to a location of TRP1.

The cassette including L-ldh may be inserted to the locus of TRP1, and in this case, L-ldh may be inserted as the TRP1 gene is deleted. The L-ldh insertion mutant strain is prepared as follows.

The KCTC12415BP strain thus obtained was plated onto a YPD agar plate (including 10 g of yeast extract, 20 g of peptone, and 20 g of glucose) and incubated for 24 hours at 30° C., and then, a colony obtained therefrom was inoculated in about 10 ml of a YPD liquid medium and cultured for about 18 hours at about 30° C. The sufficiently grown culture solution was inoculated in about 50 ml of a YPD liquid medium contained in a 250 ml-flask at a concentration of 1% (v/v) and cultured in an incubator at a rate of about 230 rpm and at 30° C.

After about 4 to 5 hours, when the $OD_{600}$ reached about 0.5, the culture was centrifuged at a rate of about 4,500 rpm for about 10 minutes to harvest cells, and the cells were resuspensed in a lithium acetate solution at a concentration of about 100 mM. Then, the cells were harvested by performing centrifugation at a rate of about 4,500 rpm for about 10 minutes, resuspensed in a lithium acetate solution at a concentration of about 1 M including 15% of glycerol, and then divided into a volume of about 100 μl each.

In order to express L-ldh, at the same time deleting TRP1, an L-ldh expression cassette including HIS3 prepared in Example 1.3.1 was mixed with 50% of polyethylene glycol and a single stranded carrier DNA and reacted in a water tub for about 1 hour at 42° C., and then, the culture solution was spread on a histidine-free minimal agar plate (including YSD, 6.7 g/L of yeast nitrogen base without amino acids, and 1.4 g/L of amino acid dropout mix (-his)) and grown for about 24 hours or more at 30° C. Ten colonies (mutant strains) grown on the plate were selected, patched onto the fresh histidin-free minimal agar plate, and at the same time, inoculated into a liquid medium including the same components contained in the histidin-free minimal agar plate to isolate the genomic DNA from the above mutant strains by using a commonly used kit (Gentra Puregene Cell kit, Qiagen, USA). PCR was performed using the isolated genomic DNA of the mutant stain as a template and primers of SEQ ID NOS: 46 and 47, and then, electrophoresis was performed on the obtained PCR product to confirm insertion of the L-ldh expression cassette. As a result, the strain thus obtained was named CEN.PK2-1D KCTC12415BPΔtrp1::ldh.

Example 2

Preparation of NDE1 Gene Deletion Cassette and Preparation of NDE1-Deleted *Saccharomyces cerevisiae* Strain (2.1) Preparation of NDE1 Gene Deletion Cassette In order to delete NDE1 gene by using a homogenous recombination method, pUC57-CCW12p-LDH-ura3HA prepared in Example 1.1.2 was used as a vector for inactivating NDE1 gene. PCR was performed using the prepared pUC57-CCW12p-LDH-ura3HA as a template and primers of SEQ ID NOS: 48 and 49.

(2.2) Preparation of *Saccharomyces cerevisiae* Strain in which NDE1 is Deleted

A mutant strain of *Saccharomyces cerevisiae* CEN.PK2-1D KCTC12415BPΔtrp1::ldh, in which nde1 gene is deleted, was prepared in the same manner as follows. The *Saccharomyces cerevisiae* CEN.PK2-1D KCTC12415BPΔtrp1::ldh thus obtained was plated onto a YPD agar plate (including 10 g of yeast extract, 20 g of peptone, and 20 g of glucose) and incubated for 24 hours at 30° C., and then, a colony obtained therefrom was inoculated in about 10 ml of a YPD liquid medium and cultured for about 18 hours at about 30° C. The sufficiently grown culture solution was inoculated in about 50 ml of a YPD liquid medium contained in a 250 ml-flask at a concentration of 1% (v/v) and cultured in an incubator at a rate of about 230 rpm and at 30° C. After about 4 to 5 hours, when the $OD_{600}$ reached about 0.5, the culture was centrifuged at a rate of about 4,500 rpm for about 10 minutes to harvest cells, and the cells were resuspensed in a lithium acetate solution at a concentration of about 100 mM. Then, the cells were harvested by performing centrifugation at a rate of about 4,500 rpm for about 10 minutes, resuspensed in a lithium acetate solution at a concentration of about 1 M including 15% of glycerol, and then divided into a volume of about 100 μl each.

In order to delete NDE1, the NDE1 deletion cassette prepared in Example 2.1 was introduced to the resuspended *Saccharomyces cerevisiae* CEN.PK2-1D KCTC12415BPΔtrp1::ldh in the same manner used in deletion of the pdc1, cyb2, and gpd1 genes. Ten colonies grown on the plate were selected to isolate the genomic DNA. PCR was performed using the isolated genomic DNA of the mutant stain as a template and primers of SEQ ID NOS: 50 and 51, and then, electrophoresis was performed on the obtained PCR product to confirm deletion of NDE1. As a result, Saccharomyces cerevisiae CEN.PK2-1D (KCTC12415BPΔtrp1::ldhΔnde1+ura3) was obtained.

Also, for additional gene deletion using the gene deletion vector, a URA3 gene as a selection marker was removed from Saccharomyces cerevisiae CEN.PK2-1D (KCTC12415BPΔtrp1::ldhΔnde1+ura3) by using the URA3 pop-out method as described above. Ten colonies grown on a plate were selected to isolate genomic DNA. In order to confirm deletion of URA3 gene by using the isolated genomic DNA of the URA3 pop-out strain as a template, PCR was performed using primers of SEQ ID NOS: 50 and 51, and then electrophoresis was performed on the obtained PCR product to confirm deletion of URA3 gene. As a result, Saccharomyces cerevisiae CEN.PK2-1D (KCTC12415BPΔtrp1::ldhΔnde1) was obtained.

Example 3

Preparation of Strain with Depressed Activity of PYC1 and/or PYC2

In order to prepare a strain with a depressed PYC1 and/or PYC2 activity, a PYC1 and/or PYC2 promoter (Ppyc1 and Ppyc2) were replaced with a promoter at a lower level of expression compared to the promoters as follows. The promoter at a lower level of expression compared to the promoter was a LEUM promoter ($P_{leum}$), a CYC1 promoter ($P_{cyc1}$), or a combination thereof. The LEUM promoter is a mutant of a LEU2 promoter, in which a LEU2 promoter is truncated.

(3.1) Preparation of $P_{leum}$ and $P_{cyc1}$ and Preparation of Recombination Vector In order to prepare a DNA fragment including a LEUM promoter ($P_{leum}$) (SEQ ID NO: 25), after extracting gDNA, which is a wild strain of Saccharomyces cerevisiae CEN.PK2-1D chromosome, by using a Genomic-tip system of Qiagen, PCR was performed using the gDNA as a template and a PCR HL premix kit (BIONEER).

As PCR for amplifying $P_{leum}$, 30 cycles of PCR was performed, each cycle including 30 seconds of denaturation at 94° C., 30 seconds of annealing at 52° C., and 30 seconds of elongation at 72° C. using primers of SEQ ID NO: 53 and SEC ID NO: 54. The PCR product was digested with EcoRI, and then the DNA fragment (hereinafter, referred to as "$P_{leum}$ cassette 1") was dissolved in 0.8% agarose gel by performing electrophoresis.

As PCR for amplifying $P_{leum}$, 30 cycles of PCR was performed, each cycle including 30 seconds of denaturation at 94° C., 30 seconds of annealing at 52° C., and 30 seconds of elongation at 72° C. using primers of SEQ ID NO: 58 and SEC ID NO: 59. The PCR product was digested with BamHI, and then the DNA fragment (hereinafter, referred to as "$P_{leum}$ cassette 2") was dissolved in 0.8% agarose gel by performing electrophoresis.

Also, in order to obtain a DNA fragment including a CYC1 promoter ($P_{cyc1}$) (SEQ ID NO: 55), after extracting gDNA, which is a wild strain of Saccharomyces cerevisiae CEN.PK2-1D chromosome, by using a Genomic-tip system of Qiagen, PCR was performed using the gDNA as a template and a PCR HL premix kit (BIONEER).

As PCR for amplifying $P_{cyc1}$, 30 cycles of PCR was performed, each cycle including 30 seconds of denaturation at 94° C., 30 seconds of annealing at 52° C., and 30 seconds of elongation at 72° C. using primers of SEQ ID NO: 56 and SEC ID NO: 57. The PCR product was digested with EcoRI, and then the DNA fragment (hereinafter, referred to as "$P_{cyc1}$ cassette 1") was dissolved in 0.8% agarose gel by performing electrophoresis.

As PCR for amplifying $P_{cyc1}$, 30 cycles of PCR was performed, each cycle including 30 seconds of denaturation at 94° C., 30 seconds of annealing at 52° C., and 30 seconds of elongation at 72° C. using primers of SEQ ID NO: 60 and SEC ID NO: 61. The PCR product was digested with BamHI, and then the DNA fragment (hereinafter, referred to as "$P_{cyc1}$ cassette 2") was dissolved in 0.8% agarose gel by performing electrophoresis.

Figure 7:
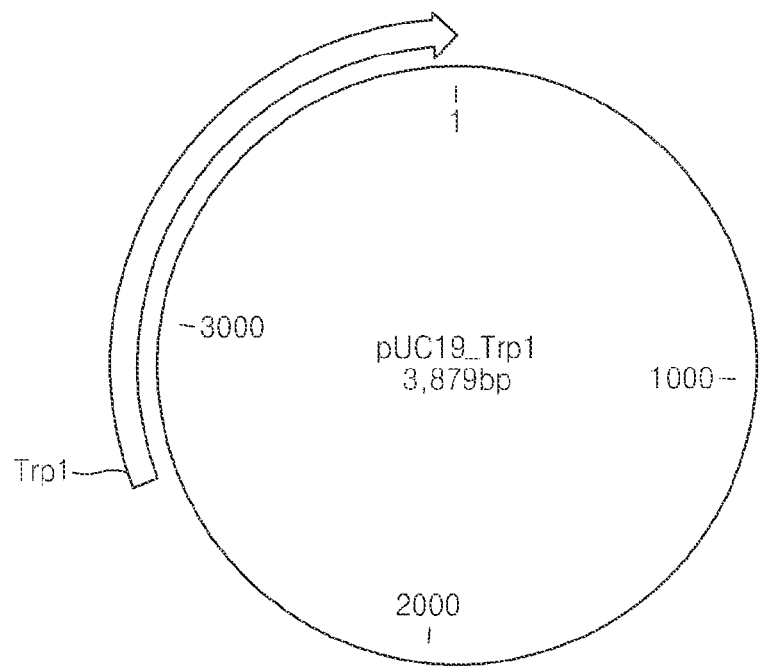
FIG. 7 is a diagram illustrating a pUC19-Trp1 vector.
Figure 9:
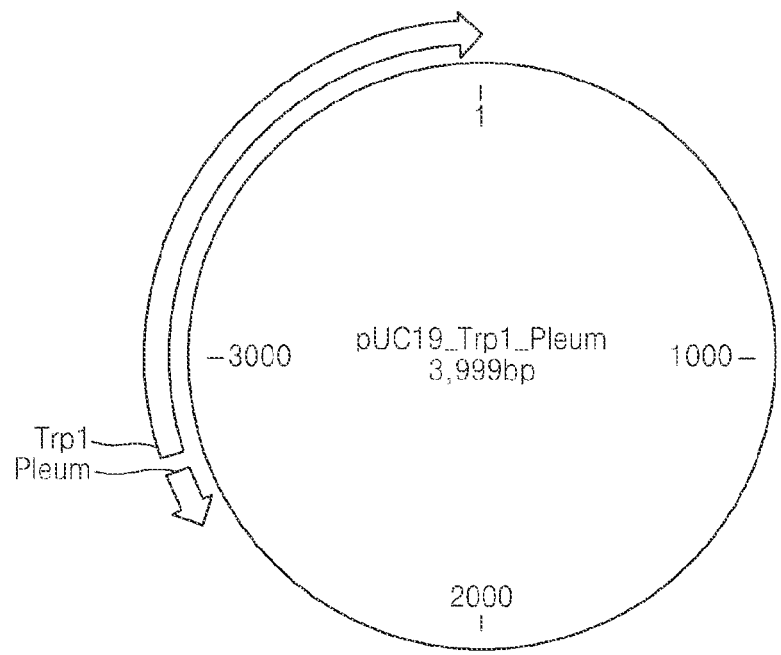
FIG. 9 is a diagram illustrating a pUC19-Trp1-$P_{leum}$ vector.

The pUC19-Trp1 vector (Appl Environ Microbiol. 2002 May; 68(5):2095-100) and the prepared $P_{leum}$ cassette 1 were treated with a restriction enzyme EcoRI and ligated to prepare a pUC19-Trp1-$P_{leum}$ vector. FIG. 7 illustrates a pUC19-Trp1 vector. FIG. 9 illustrates a pUC19-Trp1-$P_{leum}$ vector.

Figure 8:
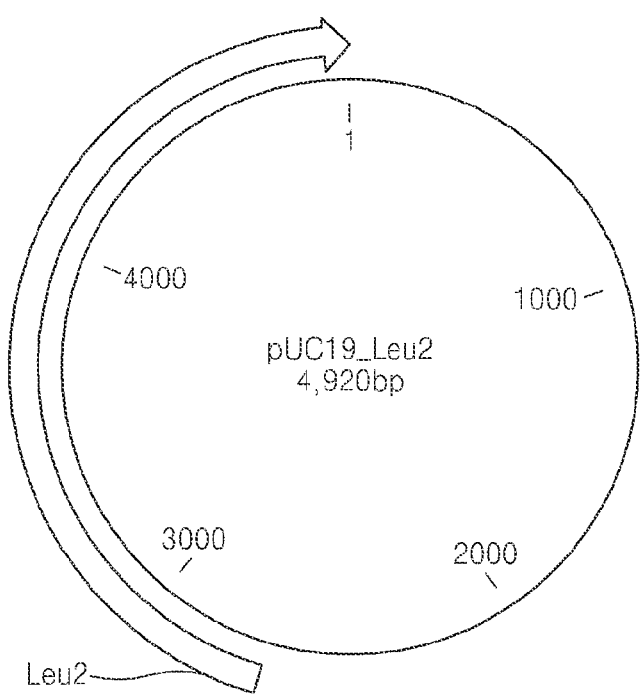
FIG. 8 is a diagram illustrating a pUC19-Leu2 vector.
Figure 11:
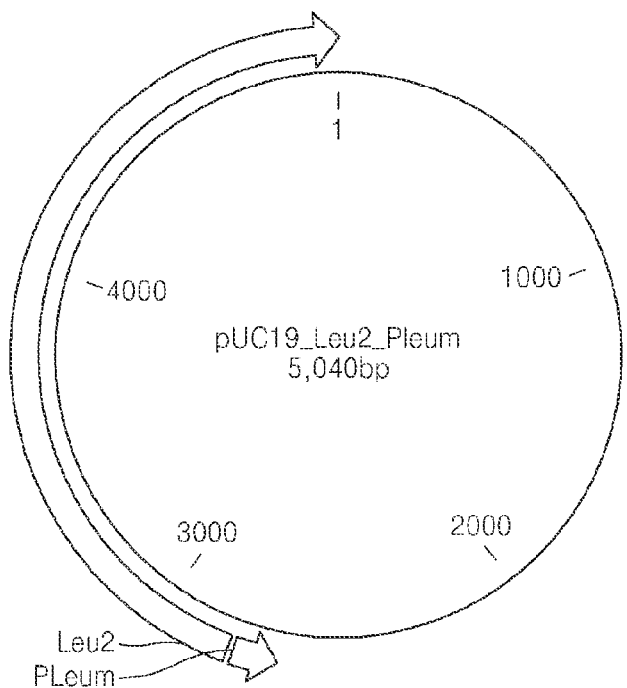
FIG. 11 is a diagram illustrating a pUC19-Leu2-$P_{leum}$ vector.

Also, the pUC19-Trp1 vector (Appl Environ Microbiol. 2002 May; 68(5):2095-100) and the prepared $P_{leum}$ cassette 2 were treated with a restriction enzyme BamHI and ligated to prepare a pUC19-Leu2-$P_{leum}$ vector. FIG. 8 illustrates a pUC19-Leu2 vector. FIG. 11 illustrates a pUC19-Leu2-$P_{leum}$ vector.

In order to prepare a strain, in which $P_{pyc1}$ is replaced with $P_{leum}$ and $P_{pyc2}$ is replaced with $P_{leum}$ as described later, the pUC19-Trp1-$P_{leum}$ vector and the pUC19-Leu2-$P_{leum}$ vector having the same $P_{leum}$ cassette and different markers were prepared.

Figure 10:
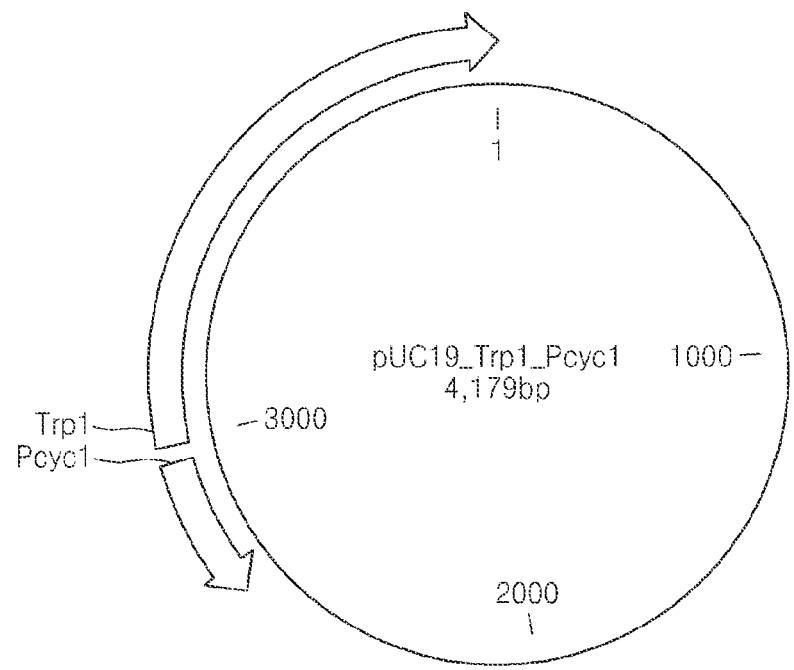
FIG. 10 is a diagram illustrating a pUC19-Trp1-$P_{cyc1}$ vector.

The pUC19-Trp1 vector (Appl Environ Microbiol. 2002 May; 68(5):2095-100) plasmid and the prepared $P_{cyc1}$ cassette 1 were treated with a restriction enzyme EcoRI and ligated to prepare a pUC19-Trp1-$P_{cyc1}$ vector. FIG. 10 illustrates the pUC19-Trp1-$P_{cyc1}$ vector.

Figure 12:
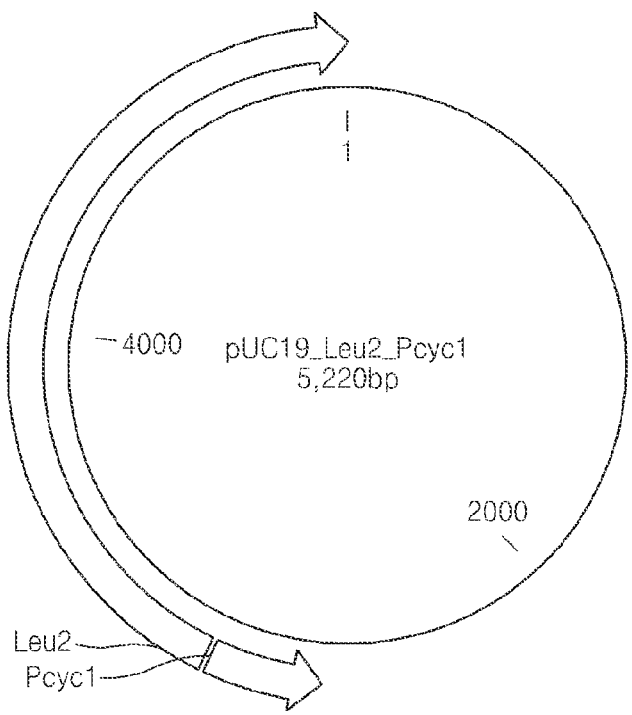
FIG. 12 is a diagram illustrating a pUC19-Leu2-$P_{cyc1}$ vector.

Also, the pUC19-Leu2 vector (Appl Environ Microbiol. 2002 May; 68(5):2095-100) plasmid and the prepared $P_{cyc1}$ cassette 2 were treated with a restriction enzyme BamHI and ligated to prepare a pUC19-Leu2-$P_{cyc1}$ vector. FIG. 12 illustrates the pUC19-Leu2-$P_{cyc1}$ vector.

(3.2) Preparation of $P_{pyc2}$ Deletion Cassette

In order to delete a $P_{pyc2}$ promoter ($P_{pyc2}$) by using a homogenous recombination method, the pUC57-ura3HA was used as a vector for inactivating a Ppyc2 promoter gene. To prepare a Ppyc2 promoter deletion cassette, PCR was performed using the prepared pUC57-ura3HA as a template and primers of SEQ ID NO: 62 and 63, and thus a $P_{pyc2}$ deletion cassette was prepared.

(3.3) Preparation of Strain with pyc1 Promoter and/or pyc2 Promoter Replaced with $P_{leum}$ and $P_{cyc1}$ Fragment (3.3.1) Preparation of pyc1 Promoter and/or pyc2 Promoter Replacement Cassette In order to replace $P_{pyc1}$ with $P_{cyc1}$ or $P_{leum}$ by using a homogenous recombination method, the pUC19-TRP1-Pcyc1 and pUC19-TRP1-Pleum were each respectively used. PCR was performed using the pUC19-TRP1-Pcyc1 as a template and primers of SEQ ID NOS: 68 and 69 to prepare a cassette for replacing $P_{pyc1}$ to $P_{cyc1}$, and PCR was performed using the pUC19-TRP1-Pleum as a template and primers of SEQ ID NOS: 68 and 70 to prepare a cassette for replacing $P_{pyc1}$ to $P_{leum}$.

In order to replace $P_{pyc2}$ with $P_{leum}$ by using a homogenous recombination method, the pUC19-LEU2-$P_{leum}$ was used. PCR was performed using the pUC19-LEU2-Pleum as a template and primers of SEQ ID NOS: 71 and 72 to prepare a cassette for replacing $P_{pyc2}$ to $P_{leum}$.

(3.3.2) Preparation of Strain in which $P_{pyc1}$ is Replaced with $P_{Leum}$

In order to replace $P_{pyc1}$ to $P_{leum}$, the replacement cassette prepared in Example 3.3.1 was mixed with 50% of polyethyleneglycol and a single stranded carrier DNA and reacted in a water tub for about 1 hour at 42° C., and then, the *S. cerevisea* CEN.PK2-1D (KCTC12415BPΔtrp1::ldhΔnde1) culture solution was plated onto a uracil-free minimal agar plate (including YSD, 6.7 g/L of yeast nitrogen base without amino acids, and 1.4 g/L of amino acid dropout mix (-ura)) in a plate and cultured for 24 hours or more at 30° C.

Ten colonies (a mutant strain) formed in the plate were selected, transferred to another uracil-free minimal agar plate, and, at the same time, cultured in a liquid medium including the same components contained in the uracil-free minimal medium to separate genome DNA from the strain by using a commonly used kit (Gentra Puregene Cell kit, Qiagen, USA). In order to confirm replacement of $P_{pyc1}$ to $P_{leum}$ by using the separated genome DNA of the mutant strain as a template, PCR was performed using primers of SEQ ID NOS: 64 and 65, and then, electrophoresis was performed on the obtained PCR product. As a result, *Saccharomyces cerevisiae* CEN.PK2-1D (KCTC12415BPΔtrp1::ldhΔnde1ΔPpyc1::Pleum) was obtained.

(3.3.3) Preparation of Strain in which $P_{pyc1}$ is Replaced with $P_{leum}$ and $P_{pyc2}$ is Replaced with $P_{cyc1}$ In order to replace $P_{pyc1}$ to $P_{leum}$ and $P_{pyc2}$ to $P_{cyc1}$, the replacement cassette prepared in Example 3.3.1 was mixed with 50% of polyethyleneglycol and a single stranded carrier DNA and reacted in a water tub for about 1 hour at 42° C., and then, the *S. cerevisea* CEN.PK2-1D (KCTC12415BPΔtrp1::ldhΔnde1ΔPpyc1::Pleum) culture solution was plated onto a uracil-free minimal agar plate (including YSD, 6.7 g/L of yeast nitrogen base without amino acids, and 1.4 g/L of amino acid dropout mix (-ura)) in a plate and cultured for 24 hours or more at 30° C. Ten colonies (a mutant strain) formed in the plate were selected, transferred to another uracil-free minimal agar plate, and, at the same time, cultured in a liquid medium including the same components contained in the uracil-free minimal medium to separate genome DNA from the strain by using a commonly used kit (Gentra Puregene Cell kit, Qiagen, USA). In order to confirm replacement of $P_{pyc2}$ to $P_{cyc1}$ by using the separated genome DNA of the mutant strain as a template, PCR was performed using primers of SEQ ID NOS: 66 and 67, and then, electrophoresis was performed on the obtained PCR product. As a result, *Saccharomyces cerevisiae* CEN.PK2-1D (KCTC12415BPΔtrp1::ldhΔnde1ΔPpyc1::PleumΔPpyc2::Pcyc1) was obtained.

(3.3.4) Preparation of Strain in which $P_{pyc1}$ is Replaced with $P_{leum}$ and $P_{pyc2}$ is Replaced with $P_{leum}$ In order to replace $P_{pyc1}$ to $P_{leum}$ and $P_{pyc2}$ to $P_{leum}$, the replacement cassette prepared in Example 3.3.1 was mixed with 50% of polyethyleneglycol and a single stranded carrier DNA and reacted in a water tub for about 1 hour at 42° C., and then, the *S. cerevisea* CEN.PK2-1D (KCTC12415BPΔtrp1::ldhΔnde1ΔPpyc1::PLeum) culture solution was plated onto a uracil-free minimal agar plate (including YSD, 6.7 g/L of yeast nitrogen base without amino acids, and 1.4 g/L of amino acid dropout mix (-ura)) in a plate and cultured for 24 hours or more at 30° C. Ten colonies (a mutant strain) formed in the plate were selected, transferred to another uracil-free minimal agar plate, and, at the same time, cultured in a liquid medium including the same components contained in the uracil-free minimal medium to separate genome DNA from the strain by using a commonly used kit (Gentra Puregene Cell kit, Qiagen, USA). In order to confirm replacement of $P_{pyc2}$ to $P_{leum}$ by using the separated genome DNA of the mutant strain as a template, PCR was performed using primers of SEQ ID NOS: 66 and 67, and then, electrophoresis was performed on the obtained PCR product. As a result, *Saccharomyces cerevisiae* CEN.PK2-1D (KCTC12415BPΔtrp1::ldhΔnde1ΔPpyc1::PleumΔPpyc2::Pleum) was obtained.

(3.3.5) Preparation of Strain in which $P_{pyc1}$ is Replaced with $P_{Cyc1}$

In order to replace $P_{pyc1}$ to $P_{cyc1}$, the replacement cassette prepared in Example 3.3.1 was mixed with 50% of polyethyleneglycol and a single stranded carrier DNA and reacted in a water tub for about 1 hour at 42° C., and then, the *S. cerevisea* CEN.PK2-1D (KCTC12415BPΔtrp1::ldhΔnde1) culture solution was plated onto a uracil-free minimal agar plate (including YSD, 6.7 g/L of yeast nitrogen base without amino acids, and 1.4 g/L of amino acid dropout mix (-ura)) in a plate and cultured for 24 hours or more at 30° C. Ten colonies (a mutant strain) formed in the plate were selected, transferred to another uracil-free minimal agar plate, and, at the same time, cultured in a liquid medium including the same components contained in the uracil-free minimal medium to separate genome DNA from the strain by using a commonly used kit (Gentra Puregene Cell kit, Qiagen, USA). In order to confirm replacement of $P_{pyc1}$ to $P_{cyc1}$ by using the separated genome DNA of the mutant strain as a template, PCR was performed using primers of SEQ ID NOS: 64 and 65, and then, electrophoresis was performed on the obtained PCR product. As a result, *Saccharomyces cerevisiae* CEN.PK2-1D (KCTC12415BPΔtrp1::ldhΔnde1ΔPpyc1::Pcyc1) was obtained.

(3.3.6) Preparation of Strain in which $P_{pyc1}$ is Replaced with $P_{cyc1}$ and $P_{pyc2}$ is Replaced with $P_{leum}$ In order to replace $P_{pyc1}$ to $P_{cyc1}$ and $P_{pyc2}$ to $P_{leum}$, the replacement cassette prepared in Example 3.3.1 was mixed with 50% of polyethyleneglycol and a single stranded carrier DNA and reacted in a water tub for about 1 hour at 42° C., and then, the *S. cerevisea* CEN.PK2-1D (KCTC12415BPΔtrp1::ldhΔnde1ΔPpyc1::Pcyc1) culture solution was plated onto a uracil-free minimal agar plate (including YSD, 6.7 g/L of yeast nitrogen base without amino acids, and 1.4 g/L of amino acid dropout mix (-ura)) in a plate and cultured for 24 hours or more at 30° C. Ten colonies (a mutant strain) formed in the plate were selected, transferred to another uracil-free minimal agar plate, and, at the same time, cultured in a liquid medium including the same components contained in the uracil-free minimal medium to separate genome DNA from the strain by using a commonly used kit (Gentra Puregene Cell kit, Qiagen, USA). In order to confirm replacement of $P_{pyc1}$ to $P_{leum}$ by using the separated genome DNA of the mutant strain as a template, PCR was performed using primers of SEQ ID NOS: 66 and 67, and then, electrophoresis was performed on the obtained PCR product to confirm replacement of $P_{pyc2}$ to $P_{cyc1}$. As a result, *Saccharomyces cerevisiae* CEN.PK2-1D (KCTC12415BPΔtrp1::ldhΔnde1ΔPpyc1::Pcyc1ΔPpyc2::Pleum) was obtained.

(3.3.7) Preparation of Strain in which $P_{pyc1}$ is Replaced with $P_{cyc1}$ and $P_{pyc2}$ is Deleted In order to replace $P_{pyc1}$ to $P_{cyc1}$ and delete $P_{pyc2}$, the $P_{pyc2}$ deletion cassette prepared in Example 3.2 was mixed with 50% of polyethyleneglycol and a single stranded carrier DNA and reacted in a water tub for about 1 hour at 42° C., and then, the *S. cerevisea* CEN.PK2-1D (KCTC12415BPΔtrp1::ldhΔnde1ΔP$_{pyc1}$::P$_{cyc1}$) culture solution was plated onto a uracil-free minimal agar plate (including YSD, 6.7 g/L of yeast nitrogen base without amino acids, and 1.4 g/L of amino acid dropout mix (-ura)) in a plate and cultured for 24 hours or more at 30° C. Ten colonies (a mutant strain) formed in the plate were selected, transferred to another uracil-free minimal agar plate, and, at the same time, cultured in a liquid medium including the same components contained in the uracil-free minimal medium to separate genome DNA from the strain by using a commonly used kit (Gentra Puregene Cell kit, Qiagen, USA). In order to confirm deletion of P$_{pyc2}$ by using the separated genome DNA of the mutant strain as a template, PCR was performed using primers of SEQ ID NOS: 66 and 67, and then, electrophoresis was performed on the obtained PCR product to confirm replacement of P$_{pyc2}$ to P$_{cyc1}$. As a result, *Saccharomyces cerevisiae* CEN.PK2-1D (KCTC12415BPΔtrp1::ldhΔnde1ΔP$_{pyc1}$::P$_{cyc1}$ΔP$_{pyc2}$) was obtained.

Example 4

Lactate Production Using Strain with Depressed pyc1 and/or pyc2 Activity and Strain with Depressed pyc1 Activity and Inactivated pyc2 Activity Each of the strains prepared in Examples 3.3.1 to 3.3.6 was spread on a YPD agar plate and incubated for 24 hours or more at 30° C., and then, a colony obtained therefrom was inoculated in about 50 ml of a YPD liquid medium including 40 g/L of glucose, and incubated in an aerobic condition for about 29.5 hours at 30° C. Fermentation was performed by measuring an amount of a cell concentration when an optical density at 600 nm (OD$_{600}$) reached 5.0 by using a spectrophotometer, discarding the supernatant thereof after performing centrifuge, resuspending the cells, and inoculating again in 50 ml of a fresh YPD including 80 g/L of glucose.

The cells were fermented in a stirring incubator maintaining 90 rpm for 24 hours at 30° C. During the fermentation, a sample was periodically obtained from the flask, and the obtained sample was centrifuged at 13,000 rpm for 10 minutes, and concentrations of metabolic products including lactate and glucose in the supernatant were analyzed by using an HPLC. An initial amount of glucose was 82.6 g/L. A yield of lactate was calculated as a percent of an amount of produced lactate production divided by an amount of consumed glucose, and the results are shown in Table 1.

As shown in Table 1, a L-lactate production of KCTC12415BPΔtrp1::ldhΔnde1ΔP$_{pyc1}$::P$_{leum}$ increased from 32.5 g/L to 35.1 g/L compared to that of KCTC12415BPΔtrp1::ldhΔnde1, and a yield of KCTC12415BPΔtrp1::ldhΔnde1ΔP$_{pyc1}$::P$_{leum}$ increased from 45.3% to 49.5% compared to that of KCTC12415BPΔtrp1::ldhΔnde1.

The lactate production of KCTC12415BPΔtrp1::ldhΔnde1ΔP$_{pyc1}$::P$_{Leum}$ΔP$_{pyc2}$::P$_{cyc1}$ increased from 32.5 g/L to 37.0 g/L compared to that of KCTC12415BPΔtrp1::ldhΔnde1, and a yield of KCTC12415BPΔtrp1::ldhΔnde1ΔP$_{pyc1}$::P$_{Leum}$ΔP$_{pyc2}$::P$_{cyc1}$ increased from 45.3% to 49.5% compared to that of KCTC12415BPΔtrp1::ldhΔnde1.

The lactate production of L-lactate production of KCTC12415BPΔtrp1::ldhΔnde1ΔP$_{pyc1}$::P$_{leum}$ΔP$_{pyc2}$::P$_{leum}$ increased from 32.5 g/L to 35.9 g/L compared to that of KCTC12415BPΔtrp1::ldhΔnde1, and a yield of KCTC12415BPΔtrp1::ldhΔnde1ΔP$_{pyc1}$::P$_{leum}$ΔP$_{pyc2}$::P$_{leum}$ increased from 45.3% to 49.9% compared to that of KCTC12415BPΔtrp1::ldhΔnde1.

The lactate production of L-lactate production of KCTC12415BPΔtrp1::ldhΔnde1ΔP$_{pyc1}$::P$_{cyc1}$ increased from 32.5 g/L to 35.3 g/L compared to that of KCTC12415BPΔtrp1::ldhΔnde1, and a yield of KCTC12415BPΔtrp1::ldhΔnde1ΔP$_{pyc1}$::P$_{cyc1}$ increased from 45.3% to 48.9% compared to that of KCTC12415BPΔtrp1::ldhΔnde1.

The lactate production of L-lactate production of KCTC12415BPΔtrp1::ldhΔnde1ΔP$_{pyc1}$::P$_{cyc1}$ΔP$_{pyc2}$::P$_{leum}$ increased from 32.5 g/L to 35.5 g/L compared to that of KCTC12415BPΔtrp1::ldhΔnde1, and a yield of KCTC12415BPΔtrp1::ldhΔnde1ΔP$_{pyc1}$::P$_{cyc1}$ΔP$_{pyc2}$::P$_{leum}$ increased from 45.3% to 47.5% compared to that of KCTC12415BPΔtrp1::ldhΔnde1.

The lactate production of L-lactate production of KCTC12415BPΔtrp1::ldhΔnde1ΔP$_{pyc1}$::P$_{cyc1}$ΔP$_{pyc2}$ increased from 32.5 g/L to 36.6 g/L compared to that of KCTC12415BPΔtrp1::ldhΔnde1, and a yield of KCTC12415BPΔtrp1::ldhΔnde1ΔP$_{pyc1}$::P$_{cyc1}$ΔP$_{pyc2}$ increased from 45.3% to 45.6% compared to that of KCTC12415BPΔtrp1::ldhΔnde1.

TABLE 1

| Strain | OD$_{600}$ | Glucose Consumption (g/L) | L-lactate production (g/L) | Yield (%) |
|---|---|---|---|---|
| KCTC12415BP Δ trp1::ldh Δ nde1 | 16.0 | 71.7 | 32.5 | 45.3 |
| KCTC12415BP Δ trp1::ldh Δ nde1 Δ Ppyc1::P$_{leum}$ | 14.7 | 69.7 | 35.1 | 49.5 |
| KCTC12415BP Δ trp1::ldh Δ nde1 Δ Ppyc1::P$_{leum}$ Δ Ppyc2::Pcyc1 | 16.3 | 74.7 | 37.0 | 49.5 |
| KCTC12415BP Δ trp1::ldh Δ nde1 Δ Ppyc1::P$_{leum}$ Δ Ppyc2::P$_{leum}$ | 15.1 | 71.8 | 35.9 | 49.9 |
| KCTC12415BP Δ trp1::ldh Δ nde1 Δ Ppyc1::Pcyc1 | 15.2 | 72.2 | 35.3 | 48.9 |
| KCTC12415BP Δ trp1::ldh Δ nde1 Δ Ppyc1::Pcyc1 Δ Ppyc2::P$_{leum}$ | 16.3 | 74.8 | 35.5 | 47.5 |
| KCTC12415BP Δ trp1::ldh Δ nde1 Δ Ppyc1::Pcyc1 Δ Ppyc2 | 17.7 | 80.2 | 36.6 | 45.6 |

Example 5

Lactate Production Using Strain with Depressed PYC1 and/or PYC2 Activity and Strain with Depressed PYC1 Activity and Inactivated PYC2 Activity KCTC12415BPΔtrp1::ldhΔnde1ΔP$_{pyc1}$::P$_{leum}$ΔP$_{pyc2}$::P$_{leum}$ from the strains prepared in Examples 3.3.2 to 3.3.7 was spread on a YPD agar plate and incubated for 24 hours or more at 30° C., and then, a colony obtained therefrom was inoculated in about 100 ml of a YPD liquid medium including 80 g/L of glucose, and incubated in an aerobic condition for about 16 hours at 30° C.

Fermentation was performed by separately inoculating 100 ml of the strain culture solution in a bioreactor containing 1 L of a synthesis medium, and the fermentation condition included initially 60 g/L of glucose and 20 g/L of yeast extract at 30° C. During the fermentation, pH was maintained at pH 5 by using 5N Ca(OH)$_2$ up to 16 hours, pH 4.5 up to 24 hours, and pH 3.0 up to 60 hours, and a concentration of glucose was maintained at 20 g/L. Additional synthesis medium components included 50 g/L of K$_2$HPO$_4$, 10 g/L of MgSO$_4$, 0.1 g/L of tryptophan, and 0.1 g/L of histidine in addition to glucose.

A cell concentration in the culture was estimated by using a spectrophotometer, samples were periodically obtained from the bioreactor during the fermentation, the samples thus obtained were centrifuged at 13,000 rpm for 10 minutes, and then metabolic products and concentration s of lactate and glucose of the supernatants were analyzed by high pressure liquid chromatography (HPLC).

As shown in Table 2, an L-lactate production of KCTC12415BPΔtrp1::ldhΔnde1ΔP$_{pyc1}$::P$_{leum}$ΔP$_{pyc2}$::P$_{leum}$ increased from 119.8 g/L to 122.8 g/L compared to that of KCTC12415BPΔtrp1::ldhΔnde1, and a yield of KCTC12415BPΔtrp1::ldhΔnde1ΔP$_{pyc1}$::P$_{leum}$ΔP$_{pyc2}$::P$_{leum}$ increased from 57.2% to 65.6% compared to that of KCTC12415BPΔtrp1::ldhΔnde1.

TABLE 2

| Strain | OD$_{600}$ | L-lactate production (g/L) | Yield (%) |
|---|---|---|---|
| KCTC12415BP Δ trp1::ldh Δ nde1 | 17.2 | 119.8 | 57.2 |
| KCTC12415BP Δ trp1::ldh Δ nde1 Δ Ppyc1::P$_{Leum}$ Δ Ppyc2::P$_{Leum}$ | 15.1 | 122.8 | 65.6 |

[Accession Number]

Research Center Name: Korean Collection for Type Cultures (KTCT)

Accession Number: KCTC 12415BP

Accession Date: May 30, 2013

As described above, according to the one or more of the above embodiments of the present invention, a yeast cell may produce lactate at a high yield, and a method of producing lactate may produce lactate at a high yield.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically engineered yeast cell comprising a mutation or deletion in a gene encoding pyruvate carboxylase 1 (PYC1), a gene encoding pyruvate carboxylase 2 (PYC2), or both, wherein the yeast cell exhibits reduced conversion of pyruvate to oxaloacetate as compared to a parent yeast cell thereof, and the yeast cell comprises a deletion or disruption mutation of a gene encoding an external mitochondrial NADH dehydrogenase.

2. The genetically engineered yeast cell of claim 1, wherein the yeast cell belongs to *Saccharomyces* genus, *Kluyveromyces* genus, *Candida* genus, *Pichia* genus, *Issatchenkia* genus, *Debaryomyces* genus, *Zygosaccharomyces* genus, *Shizosaccharomyces* genus, or *Saccharomycopsis* genus.

3. The genetically engineered yeast cell of claim 1, wherein the yeast cell comprises a first mutation in the gene encoding PYC1, and a second mutation in the gene encoding PYC2.

4. The genetically engineered yeast cell of claim 3, wherein the first mutation is a deletion or disruption mutation of PYC1, and the second mutation is a deletion or disruption mutation of PYC2.

5. The genetically engineered yeast cell of claim 1, wherein the PYC1 and PYC2 each have 95% or more sequence identity with amino acid sequences of SEQ ID NOS: 1 and 2, respectively.

6. The genetically engineered yeast cell of claim 1, wherein the genetically engineered yeast cell comprises a gene comprising SEQ ID NO: 3 that encodes PYC1, and a gene comprising SEQ ID NO: 4 that encodes PYC2.

7. The genetically engineered yeast cell of claim 1, wherein the yeast cell comprises
a substitution, addition, or deletion mutation in a gene, or deletion of a part or all of a gene that encodes PYC1, a gene that encodes PYC2, or both, which inactivates or reduces the activity of PYC1 and/or PYC2 as compared to the activity of PYC1 and/or PYC2 in a parent yeast cell of the genetically engineered yeast cell;
a modification of a gene expression control sequence of a gene that encodes PYC1, a gene that encodes PYC2, or both, which modification inactivates or reduces the activity of PYC1 and/or PYC2 as compared to the activity of PYC1 and/or PYC2 in a parent yeast cell of the genetically engineered yeast cell;
or a decreased copy number of a gene that encodes pyruvate carboxylase 1 (PYC1), a gene that encodes pyruvate carboxylase 2 (PYC2), or both, as compared to the copy number of the gene in a non-genetically engineered yeast cell of the same type, which reduces the activity of the polypeptide as compared to the activity of the polypeptide in a parent yeast cell of the genetically engineered yeast cell.

8. The genetically engineered yeast cell of claim 1, wherein the yeast cell comprises a promoter operably connected to the coding region of the gene encoding PYC1, gene encoding PYC2, or both, wherein the promoter is a LEUM promoter, a CYC1 promoter, a TEF1 promoter, a GPC promoter, or a GAL promoter, and the yeast cell exhibits a lower level of expression of PYC1 and/or PYC2 as compared to that of a parent yeast cell.

9. The genetically engineered yeast cell of claim 1, wherein the yeast cell further comprises a deletion or disruption mutation of a gene encoding pyruvate decarboxylase, a gene encoding lactate cytochrome-c oxidoreductase, a gene encoding glycerol-3-phosphate dehydrogenase, or a combination thereof.

10. The genetically engineered yeast cell of claim 9, wherein the gene encoding pyruvate decarboxylase, the gene encoding lactate cytochrome-c oxidoreductase, the gene encoding glycerol-3-phosphate dehydrogenase, and the gene encoding external mitochondria NADH dehydrogenase, each encode a polypeptide comprising an amino acid sequence that is at least 95% identical to SEQ ID NOS: 5, 7, 9, and 11, respectively.

11. The genetically engineered yeast cell of claim 9, wherein a gene that encodes pyruvate decarboxylase, a gene that encodes lactate cytochrome-c oxidoreductase, a gene that encodes glycerol-3-phosphate dehydrogenase, and a gene that encodes the external mitochondria NADH dehydrogenase, have nucleotide sequences of SEQ ID NOs: 6, 8, 10, and 13 respectively.

12. The genetically engineered yeast cell of claim 1, wherein the yeast cell comprises an exogenous gene that encodes lactate dehydrogenase.

13. The genetically engineered yeast cell of claim 1, wherein the yeast comprises a heterologous gene that encodes lactate dehydrogenase.

14. A method of producing lactate, the method comprising:
culturing the yeast cell of claim 1 in a cell culture medium, whereby the yeast cell produces lactate; and
collecting lactate from the cell culture medium.

15. The method of claim 14, wherein the culturing is performed under anaerobic conditions.

16. A method of preparing a genetically engineered yeast cell of claim 1 from a parent yeast cell comprising mutating or deleting a gene encoding pyruvate carboxylase 1 (PYC1), a gene encoding pyruvate carboxylase 2 (PYC2), or both, in the parent yeast cell to reduce conversion of pyruvate to oxaloacetate, and deleting or disrupting a gene encoding an external mitochondrial NADH dehydrogenase in the parent yeast cell, to provide the genetically engineered yeast cell.

* * * * *

SEQUENCE LISTING

```
<160> NUMBER OF SEQ ID NOS: 73

<210> SEQ ID NO 1
<211> LENGTH: 1178
<212> TYPE: PRT
<213> ORGANISM: Saccharomyces cerevisiae

<400> SEQUENCE: 1

Met Ser Gln Arg Lys Phe Ala Gly Leu Arg Asp Asn Phe Asn Leu Leu
 1               5                   10                  15

Gly Glu Lys Asn Lys Ile Leu Val Ala Asn Arg Gly Glu Ile Pro Ile
            20                  25                  30
```

```
Arg Ile Phe Arg Thr Ala His Glu Leu Ser Met Gln Thr Val Ala Ile
            35                  40                  45
Tyr Ser His Glu Asp Arg Leu Ser Thr His Lys Gln Lys Ala Asp Glu
    50                  55                  60
Ala Tyr Val Ile Gly Glu Val Gly Gln Tyr Thr Pro Val Gly Ala Tyr
65                  70                  75                  80
Leu Ala Ile Asp Glu Ile Ile Ser Ile Ala Gln Lys His Gln Val Asp
                85                  90                  95
Phe Ile His Pro Gly Tyr Gly Phe Leu Ser Glu Asn Ser Glu Phe Ala
            100                 105                 110
Asp Lys Val Val Lys Ala Gly Ile Thr Trp Ile Gly Pro Pro Ala Glu
        115                 120                 125
Val Ile Asp Ser Val Gly Asp Lys Val Ser Ala Arg Asn Leu Ala Ala
    130                 135                 140
Lys Ala Asn Val Pro Thr Val Pro Gly Thr Pro Gly Pro Ile Glu Thr
145                 150                 155                 160
Val Glu Glu Ala Leu Asp Phe Val Asn Glu Tyr Gly Tyr Pro Val Ile
                165                 170                 175
Ile Lys Ala Ala Phe Gly Gly Gly Gly Arg Gly Met Arg Val Val Arg
            180                 185                 190
Glu Gly Asp Asp Val Ala Asp Ala Phe Gln Arg Ala Thr Ser Glu Ala
        195                 200                 205
Arg Thr Ala Phe Gly Asn Gly Thr Cys Phe Val Glu Arg Phe Leu Asp
    210                 215                 220
Lys Pro Lys His Ile Glu Val Gln Leu Leu Ala Asp Asn His Gly Asn
225                 230                 235                 240
Val Val His Leu Phe Glu Arg Asp Cys Ser Val Gln Arg Arg His Gln
                245                 250                 255
Lys Val Val Glu Val Ala Pro Ala Lys Thr Leu Pro Arg Glu Val Arg
            260                 265                 270
Asp Ala Ile Leu Thr Asp Ala Val Lys Leu Ala Lys Glu Cys Gly Tyr
        275                 280                 285
Arg Asn Ala Gly Thr Ala Glu Phe Leu Val Asp Asn Gln Asn Arg His
    290                 295                 300
Tyr Phe Ile Glu Ile Asn Pro Arg Ile Gln Val Glu His Thr Ile Thr
305                 310                 315                 320
Glu Glu Ile Thr Gly Ile Asp Ile Val Ala Ala Gln Ile Gln Ile Ala
                325                 330                 335
Ala Gly Ala Ser Leu Pro Gln Leu Gly Leu Phe Gln Asp Lys Ile Thr
            340                 345                 350
Thr Arg Gly Phe Ala Ile Gln Cys Arg Ile Thr Thr Glu Asp Pro Ala
        355                 360                 365
Lys Asn Phe Gln Pro Asp Thr Gly Arg Ile Glu Val Tyr Arg Ser Ala
    370                 375                 380
Gly Gly Asn Gly Val Arg Leu Asp Gly Gly Asn Ala Tyr Ala Gly Thr
385                 390                 395                 400
Ile Ile Ser Pro His Tyr Asp Ser Met Leu Val Lys Cys Ser Cys Ser
                405                 410                 415
Gly Ser Thr Tyr Glu Ile Val Arg Arg Lys Met Ile Arg Ala Leu Ile
            420                 425                 430
Glu Phe Arg Ile Arg Gly Val Lys Thr Asn Ile Pro Phe Leu Leu Thr
        435                 440                 445
```

```
Leu Leu Thr Asn Pro Val Phe Ile Glu Gly Thr Tyr Trp Thr Thr Phe
    450                 455                 460

Ile Asp Asp Thr Pro Gln Leu Phe Gln Met Val Ser Ser Gln Asn Arg
465                 470                 475                 480

Ala Gln Lys Leu Leu His Tyr Leu Ala Asp Val Ala Val Asn Gly Ser
                485                 490                 495

Ser Ile Lys Gly Gln Ile Gly Leu Pro Lys Leu Lys Ser Asn Pro Ser
            500                 505                 510

Val Pro His Leu His Asp Ala Gln Gly Asn Val Ile Asn Val Thr Lys
        515                 520                 525

Ser Ala Pro Pro Ser Gly Trp Arg Gln Val Leu Leu Glu Lys Gly Pro
530                 535                 540

Ala Glu Phe Ala Arg Gln Val Arg Gln Phe Asn Gly Thr Leu Leu Met
545                 550                 555                 560

Asp Thr Thr Trp Arg Asp Ala His Gln Ser Leu Leu Ala Thr Arg Val
                565                 570                 575

Arg Thr His Asp Leu Ala Thr Ile Ala Pro Thr Thr Ala His Ala Leu
            580                 585                 590

Ala Gly Arg Phe Ala Leu Glu Cys Trp Gly Gly Ala Thr Phe Asp Val
        595                 600                 605

Ala Met Arg Phe Leu His Glu Asp Pro Trp Glu Arg Leu Arg Lys Leu
610                 615                 620

Arg Ser Leu Val Pro Asn Ile Pro Phe Gln Met Leu Leu Arg Gly Ala
625                 630                 635                 640

Asn Gly Val Ala Tyr Ser Ser Leu Pro Asp Asn Ala Ile Asp His Phe
                645                 650                 655

Val Lys Gln Ala Lys Asp Asn Gly Val Asp Ile Phe Arg Val Phe Asp
            660                 665                 670

Ala Leu Asn Asp Leu Glu Gln Leu Lys Val Gly Val Asp Ala Val Lys
        675                 680                 685

Lys Ala Gly Gly Val Val Glu Ala Thr Val Cys Phe Ser Gly Asp Met
690                 695                 700

Leu Gln Pro Gly Lys Lys Tyr Asn Leu Asp Tyr Tyr Leu Glu Ile Ala
705                 710                 715                 720

Glu Lys Ile Val Gln Met Gly Thr His Ile Leu Gly Ile Lys Asp Met
                725                 730                 735

Ala Gly Thr Met Lys Pro Ala Ala Ala Lys Leu Leu Ile Gly Ser Leu
            740                 745                 750

Arg Ala Lys Tyr Pro Asp Leu Pro Ile His Val His Thr His Asp Ser
        755                 760                 765

Ala Gly Thr Ala Val Ala Ser Met Thr Ala Cys Ala Leu Ala Gly Ala
770                 775                 780

Asp Val Val Asp Val Ala Ile Asn Ser Met Ser Gly Leu Thr Ser Gln
785                 790                 795                 800

Pro Ser Ile Asn Ala Leu Leu Ala Ser Leu Glu Gly Asn Ile Asp Thr
                805                 810                 815

Gly Ile Asn Val Glu His Val Arg Glu Leu Asp Ala Tyr Trp Ala Glu
            820                 825                 830

Met Arg Leu Leu Tyr Ser Cys Phe Glu Ala Asp Leu Lys Gly Pro Asp
        835                 840                 845

Pro Glu Val Tyr Gln His Glu Ile Pro Gly Gly Gln Leu Thr Asn Leu
850                 855                 860

Leu Phe Gln Ala Gln Gln Leu Gly Leu Gly Glu Gln Trp Ala Glu Thr
```

```
            865                 870                 875                 880
Lys Arg Ala Tyr Arg Glu Ala Asn Tyr Leu Leu Gly Asp Ile Val Lys
                885                 890                 895
Val Thr Pro Thr Ser Lys Val Val Gly Asp Leu Ala Gln Phe Met Val
                900                 905                 910
Ser Asn Lys Leu Thr Ser Asp Asp Val Arg Arg Leu Ala Asn Ser Leu
                915                 920                 925
Asp Phe Pro Asp Ser Val Met Asp Phe Phe Glu Gly Leu Ile Gly Gln
                930                 935                 940
Pro Tyr Gly Gly Phe Pro Glu Pro Phe Arg Ser Asp Val Leu Arg Asn
945                 950                 955                 960
Lys Arg Arg Lys Leu Thr Cys Arg Pro Gly Leu Glu Leu Glu Pro Phe
                965                 970                 975
Asp Leu Glu Lys Ile Arg Glu Asp Leu Gln Asn Arg Phe Gly Asp Val
                980                 985                 990
Asp Glu Cys Asp Val Ala Ser Tyr Asn Met Tyr Pro Arg Val Tyr Glu
                995                 1000                1005
Asp Phe Gln Lys Met Arg Glu Thr Tyr Gly Asp Leu Ser Val Leu Pro
            1010                1015                1020
Thr Arg Ser Phe Leu Ser Pro Leu Glu Thr Asp Glu Ile Glu Val
1025                1030                1035                1040
Val Ile Glu Gln Gly Lys Thr Leu Ile Ile Lys Leu Gln Ala Val Gly
                1045                1050                1055
Asp Leu Asn Lys Lys Thr Gly Glu Arg Glu Val Tyr Phe Asp Leu Asn
                1060                1065                1070
Gly Glu Met Arg Lys Ile Arg Val Ala Asp Arg Ser Gln Lys Val Glu
                1075                1080                1085
Thr Val Thr Lys Ser Lys Ala Asp Met His Asp Pro Leu His Ile Gly
                1090                1095                1100
Ala Pro Met Ala Gly Val Ile Val Glu Val Lys Val His Lys Gly Ser
1105                1110                1115                1120
Leu Ile Lys Lys Gly Gln Pro Val Ala Val Leu Ser Ala Met Lys Met
                1125                1130                1135
Glu Met Ile Ile Ser Ser Pro Ser Asp Gly Gln Val Lys Glu Val Phe
                1140                1145                1150
Val Ser Asp Gly Glu Asn Val Asp Ser Ser Leu Leu Val Leu Leu
                1155                1160                1165
Glu Asp Gln Val Pro Val Glu Thr Lys Ala
            1170                1175

<210> SEQ ID NO 2
<211> LENGTH: 1180
<212> TYPE: PRT
<213> ORGANISM: Saccharomyces cerevisiae

<400> SEQUENCE: 2

Met Ser Ser Ser Lys Lys Leu Ala Gly Leu Arg Asp Asn Phe Ser Leu
1               5                   10                  15
Leu Gly Glu Lys Asn Lys Ile Leu Val Ala Asn Arg Gly Glu Ile Pro
                20                  25                  30
Ile Arg Ile Phe Arg Ser Ala His Glu Leu Ser Met Arg Thr Ile Ala
            35                  40                  45
Ile Tyr Ser His Glu Asp Arg Leu Ser Met His Arg Leu Lys Ala Asp
        50                  55                  60
```

```
Glu Ala Tyr Val Ile Gly Glu Glu Gly Gln Tyr Thr Pro Val Gly Ala
 65                  70                  75                  80

Tyr Leu Ala Met Asp Glu Ile Ile Glu Ile Ala Lys Lys His Lys Val
                 85                  90                  95

Asp Phe Ile His Pro Gly Tyr Gly Phe Leu Ser Glu Asn Ser Glu Phe
                100                 105                 110

Ala Asp Lys Val Val Lys Ala Gly Ile Thr Trp Ile Gly Pro Pro Ala
            115                 120                 125

Glu Val Ile Asp Ser Val Gly Asp Lys Val Ser Ala Arg His Leu Ala
        130                 135                 140

Ala Arg Ala Asn Val Pro Thr Val Pro Gly Thr Pro Gly Pro Ile Glu
145                 150                 155                 160

Thr Val Gln Glu Ala Leu Asp Phe Val Asn Glu Tyr Gly Tyr Pro Val
                165                 170                 175

Ile Ile Lys Ala Ala Phe Gly Gly Gly Gly Arg Gly Met Arg Val Val
                180                 185                 190

Arg Glu Gly Asp Asp Val Ala Asp Ala Phe Gln Arg Ala Thr Ser Glu
            195                 200                 205

Ala Arg Thr Ala Phe Gly Asn Gly Thr Cys Phe Val Glu Arg Phe Leu
        210                 215                 220

Asp Lys Pro Lys His Ile Glu Val Gln Leu Leu Ala Asp Asn His Gly
225                 230                 235                 240

Asn Val Val His Leu Phe Glu Arg Asp Cys Ser Val Gln Arg Arg His
                245                 250                 255

Gln Lys Val Val Glu Val Ala Pro Ala Lys Thr Leu Pro Arg Glu Val
                260                 265                 270

Arg Asp Ala Ile Leu Thr Asp Ala Val Lys Leu Ala Lys Val Cys Gly
            275                 280                 285

Tyr Arg Asn Ala Gly Thr Ala Glu Phe Leu Val Asp Asn Gln Asn Arg
        290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ser Ala Gln Ile Gln Ile
                325                 330                 335

Ala Ala Gly Ala Thr Leu Thr Gln Leu Gly Leu Leu Gln Asp Lys Ile
            340                 345                 350

Thr Thr Arg Gly Phe Ser Ile Gln Cys Arg Ile Thr Thr Glu Asp Pro
        355                 360                 365

Ser Lys Asn Phe Gln Pro Asp Thr Gly Arg Leu Glu Val Tyr Arg Ser
370                 375                 380

Ala Gly Gly Asn Gly Val Arg Leu Asp Gly Gly Asn Ala Tyr Ala Gly
                385                 390                 395                 400

Ala Thr Ile Ser Pro His Tyr Asp Ser Met Leu Val Lys Cys Ser Cys
            405                 410                 415

Ser Gly Ser Thr Tyr Glu Ile Val Arg Arg Lys Met Ile Arg Ala Leu
        420                 425                 430

Ile Glu Phe Arg Ile Arg Gly Val Lys Thr Asn Ile Pro Phe Leu Leu
    435                 440                 445

Thr Leu Leu Thr Asn Pro Val Phe Ile Glu Gly Thr Tyr Trp Thr Thr
            450                 455                 460

Phe Ile Asp Asp Thr Pro Gln Leu Phe Gln Met Val Ser Ser Gln Asn
465                 470                 475                 480

Arg Ala Gln Lys Leu Leu His Tyr Leu Ala Asp Leu Ala Val Asn Gly
```

```
                485                 490                 495
Ser Ser Ile Lys Gly Gln Ile Gly Leu Pro Lys Leu Lys Ser Asn Pro
            500                 505                 510

Ser Val Pro His Leu His Asp Ala Gln Gly Asn Val Ile Asn Val Thr
            515                 520                 525

Lys Ser Ala Pro Pro Ser Gly Trp Arg Gln Val Leu Leu Glu Lys Gly
            530                 535                 540

Pro Ser Glu Phe Ala Lys Gln Val Arg Gln Phe Asn Gly Thr Leu Leu
545                 550                 555                 560

Met Asp Thr Thr Trp Arg Asp Ala His Gln Ser Leu Leu Ala Thr Arg
                565                 570                 575

Val Arg Thr His Asp Leu Ala Thr Ile Ala Pro Thr Thr Ala His Ala
            580                 585                 590

Leu Ala Gly Ala Phe Ala Leu Glu Cys Trp Gly Gly Ala Thr Phe Asp
            595                 600                 605

Val Ala Met Arg Phe Leu His Glu Asp Pro Trp Glu Arg Leu Arg Lys
            610                 615                 620

Leu Arg Ser Leu Val Pro Asn Ile Pro Phe Gln Met Leu Leu Arg Gly
625                 630                 635                 640

Ala Asn Gly Val Ala Tyr Ser Ser Leu Pro Asp Asn Ala Ile Asp His
                645                 650                 655

Phe Val Lys Gln Ala Lys Asp Asn Gly Val Asp Ile Phe Arg Val Phe
            660                 665                 670

Asp Ala Leu Asn Asp Leu Glu Gln Leu Lys Val Gly Val Asn Ala Val
            675                 680                 685

Lys Lys Ala Gly Gly Val Val Glu Ala Thr Val Cys Tyr Ser Gly Asp
            690                 695                 700

Met Leu Gln Pro Gly Lys Lys Tyr Asn Leu Asp Tyr Tyr Leu Glu Val
705                 710                 715                 720

Val Glu Lys Ile Val Gln Met Gly Thr His Ile Leu Gly Ile Lys Asp
                725                 730                 735

Met Ala Gly Thr Met Lys Pro Ala Ala Ala Lys Leu Leu Ile Gly Ser
            740                 745                 750

Leu Arg Thr Arg Tyr Pro Asp Leu Pro Ile His Val His Ser His Asp
            755                 760                 765

Ser Ala Gly Thr Ala Val Ala Ser Met Thr Ala Cys Ala Leu Ala Gly
            770                 775                 780

Ala Asp Val Val Asp Val Ala Ile Asn Ser Met Ser Gly Leu Thr Ser
785                 790                 795                 800

Gln Pro Ser Ile Asn Ala Leu Leu Ala Ser Leu Glu Gly Asn Ile Asp
                805                 810                 815

Thr Gly Ile Asn Val Glu His Val Arg Glu Leu Asp Ala Tyr Trp Ala
            820                 825                 830

Glu Met Arg Leu Leu Tyr Ser Cys Phe Glu Ala Asp Leu Lys Gly Pro
            835                 840                 845

Asp Pro Glu Val Tyr Gln His Glu Ile Pro Gly Gly Gln Leu Thr Asn
            850                 855                 860

Leu Leu Phe Gln Ala Gln Gln Leu Gly Leu Gly Glu Gln Trp Ala Glu
865                 870                 875                 880

Thr Lys Arg Ala Tyr Arg Glu Ala Asn Tyr Leu Leu Gly Asp Ile Val
                885                 890                 895

Lys Val Thr Pro Thr Ser Lys Val Val Gly Asp Leu Ala Gln Phe Met
            900                 905                 910
```

```
Val Ser Asn Lys Leu Thr Ser Asp Asp Ile Arg Arg Leu Ala Asn Ser
    915                 920                 925

Leu Asp Phe Pro Asp Ser Val Met Asp Phe Phe Glu Gly Leu Ile Gly
    930                 935                 940

Gln Pro Tyr Gly Gly Phe Pro Glu Pro Leu Arg Ser Asp Val Leu Arg
945                 950                 955                 960

Asn Lys Arg Arg Lys Leu Thr Cys Arg Pro Gly Leu Glu Leu Glu Pro
                965                 970                 975

Phe Asp Leu Glu Lys Ile Arg Glu Asp Leu Gln Asn Arg Phe Gly Asp
            980                 985                 990

Ile Asp Glu Cys Asp Val Ala Ser Tyr Asn Met Tyr Pro Arg Val Tyr
        995                 1000                1005

Glu Asp Phe Gln Lys Ile Arg Glu Thr Tyr Gly Asp Leu Ser Val Leu
    1010                1015                1020

Pro Thr Lys Asn Phe Leu Ala Pro Ala Glu Pro Asp Glu Glu Ile Glu
1025                1030                1035                1040

Val Thr Ile Glu Gln Gly Lys Thr Leu Ile Ile Lys Leu Gln Ala Val
                1045                1050                1055

Gly Asp Leu Asn Lys Lys Thr Gly Gln Arg Glu Val Tyr Phe Glu Leu
            1060                1065                1070

Asn Gly Glu Leu Arg Lys Ile Arg Val Ala Asp Lys Ser Gln Asn Ile
        1075                1080                1085

Gln Ser Val Ala Lys Pro Lys Ala Asp Val His Asp Thr His Gln Ile
    1090                1095                1100

Gly Ala Pro Met Ala Gly Val Ile Ile Glu Val Lys Val His Lys Gly
1105                1110                1115                1120

Ser Leu Val Lys Lys Gly Glu Ser Ile Ala Val Leu Ser Ala Met Lys
                1125                1130                1135

Met Glu Met Val Val Ser Ser Pro Ala Asp Gly Gln Val Lys Asp Val
            1140                1145                1150

Phe Ile Lys Asp Gly Glu Ser Val Asp Ala Ser Asp Leu Leu Val Val
        1155                1160                1165

Leu Glu Glu Glu Thr Leu Pro Pro Ser Gln Lys Lys
    1170                1175                1180

<210> SEQ ID NO 3
<211> LENGTH: 3537
<212> TYPE: DNA
<213> ORGANISM: Saccharomyces cerevisiae

<400> SEQUENCE: 3
atgtcgcaaa gaaaattcgc cggcttgaga gataacttca atctcttggg tgaaagaac      60 aaaatattgg tggctaatag aggagaaatt ccaatcagaa ttttcgtac cgctcatgaa     120 ctgtctatgc agacggtagc tatatattct catgaagatc gtctttcaac gcacaaacaa    180
aaggctgacg aagcatacgt cataggtgaa gtaggccaat ataccccgt cggcgcttat    240 ttggccattg acgaaatcat ttccattgcc caaaacacc aggtagattt catccatcca     300
ggttatgggt tcttgtctga aaattcggaa tttgccgaca agtagtgaa ggccggtatc     360 acttggattg gccctccagc tgaagttatt gactccgtgg gtgataaggt ctcagctaga    420
aacctggcag caaaagctaa tgtgcccacc gttcctggta caccaggtcc tatagaaact    480
gtagaggaag cacttgactt cgtcaatgaa tacggctacc cggtgatcat taaggccgcc    540
tttggtggtg gtggtagagg tatgagagtc gttagagaag gtgacgacgt ggcagatgcc    600
```

```
tttcaacgtg ctacctccga agcccgtact gccttcggta atggtacctg ctttgtggaa    660
agattcttgg acaagccaaa gcatattgaa gttcaattgt tggccgataa ccacggaaac    720
gtggttcatc ttttcgaaag agactgttcc gtgcagagaa gacaccaaaa ggttgtcgaa    780
gtggccccag caaagacttt accccgtgaa gtccgtgacg ccattttgac agatgcagtt    840
aaattggcca agagtgtgg ctacagaaat gcgggtactg ctgaattctt ggttgataac    900
caaaatagac actatttcat tgaaattaat ccaagaatcc aagtggaaca taccatcaca    960
gaagaaatta ccggtataga tattgtggcg gctcagatcc aaattgcggc aggtgcctct   1020
ctaccccagc tgggcctatt ccaggacaaa attacgactc gtggctttgc cattcagtgc   1080
cgtattacca cggaagaccc tgctaagaac ttccaaccag ataccggtag aatagaagtg   1140
taccgttctg caggtggtaa tggtgttaga ctggatggtg gtaacgccta tgcaggaaca   1200
ataatctcac ctcattacga ctcaatgctg gtcaaatgct catgctccgg ttccacctac   1260
gaaatcgttc gtagaaaaat gattcgtgca ttaatcgagt tcagaattag aggtgtcaag   1320
accaacattc ccttcctatt gactctttttg accaatccag tatttattga gggtacatac   1380
tggacgactt ttattgacga caccccacaa ctgttccaaa tggtttcatc acaaaacaga   1440
gcccaaaaac ttttacatta cctcgccgac gtggcagtca atggttcatc tatcaagggt   1500
caaattggct tgccaaaatt aaaatcaaat ccaagtgtcc cccatttgca cgatgctcag   1560
ggcaatgtca tcaacgttac aaagtctgca ccaccatccg gatggaggca agtgctacta   1620 gaaaagggc cagctgaatt tgccagacaa gttagacagt tcaatggtac tttattgatg   1680
gacaccacct ggagagacgc tcatcaatct ctacttgcaa caagagtcag aacccacgat   1740
ttggctacaa tcgctccaac aaccgcacat gcccttgcag gtcgtttcgc cttagaatgt   1800
tggggtggtg ccacattcga tgttgcaatg agattttttgc atgaggatcc atgggaacgt   1860 ttgagaaaaat taagatctct ggtgcctaat attccattcc aaatgttatt gcgtggtgcc   1920
aatggtgtgg cttattcttc attgcctgac aatgctattg accatttcgt caagcaagcc   1980
aaggataatg tgttgatat atttagagtc tttgatgcct taaatgactt ggaacaattg   2040
aaggtcggtg tagatgctgt gaagaaggca ggtggtgttg tagaagccac tgtttgtttc   2100
tctggggata tgcttcagcc aggcaagaaa tacaatttgg attactactt ggaaattgct   2160
gaaaaaattg tccaaatggg cactcatatc ctgggtatca agatatggc aggtaccatg   2220 aagccagcag ctgccaaact actgattgga tctttgaggg ctaagtaccc tgatctccca   2280
atacatgttc acactcacga ttctgcaggt actgctgttg catcaatgac tgcgtgtgct   2340
ctggcgggcg ccgatgtcgt tgatgttgcc atcaactcaa tgtctggttt aacttcacaa   2400
ccatcaatca atgctctgtt ggcttcatta aaggtaata ttgacactgg tattaacgtt   2460
gagcatgtcc gtgaactaga tgcatattgg gcagagatga gattgttata ctcttgtttc   2520
gaggctgact tgaagggccc agatccagaa gtttatcaac atgaaatccc aggtggtcaa   2580
ttgacaaact tgttgtttca agcccaacaa ttgggtcttg agaacaatg ggccgaaaca   2640 aaaagagctt acagagaagc caattattta ttgggtgata ttgtcaaagt taccccaact   2700
tcgaaggtcg ttggtgatct ggcacaattt atggtctcca ataaattaac ttccgatgat   2760
gtgagacgcc tggctaattc ttttggattc cctgactctg ttatggattt cttcgaaggc   2820
ttaatcggcc aaccatatgg tgggttccca gaaccattta gatcagacgt tttaaggaac   2880
aagagaagaa agttgacttg tcgtccaggc ctggaactag agccatttga tctcgaaaaa   2940
```

-continued
attagagaag acttgcagaa tagatttggt gatgttgatg agtgcgacgt tgcttcttat 3000
aacatgtacc caagagttta tgaagacttc caaaagatga gagaaacgta tggtgattta 3060
tctgtattgc caacaagaag ctttttgtct ccactagaga ctgacgaaga aattgaagtt 3120
gtaatcgaac aaggtaaaac gctaattatc aagctacagg ctgtgggtga tttgaacaaa 3180
aagaccggtg aaagagaagt ttactttgat ttgaatggtg aaatgagaaa aattcgtgtt 3240
gctgacagat cacaaaaagt ggaaactgtt actaaatcca aagcagacat gcatgatcca 3300
ttacacattg gtgcaccaat ggcaggtgtc attgttgaag ttaaagttca taaaggatca 3360
ctaataaaga agggccaacc tgtagccgta ttaagcgcca tgaaaatgga aatgattata 3420
tcttctccat ccgatggaca agttaaagaa gtgtttgtct ctgatggtga aaatgtggac 3480
tcttctgatt tattagttct attagaagac caagttcctg ttgaaactaa ggcatga 3537

<210> SEQ ID NO 4
<211> LENGTH: 3543
<212> TYPE: DNA
<213> ORGANISM: Saccharomyces cerevisiae

<400> SEQUENCE: 4
atgagcagta gcaagaaatt ggccggtctt agggacaatt tcagtttgct cggcgaaaag 60
aataagatct tggtcgccaa tagaggtgaa attccgatta gaatttttag atctgctcat 120
gagctgtcta tgagaaccat cgccatatac tcccatgagg accgtctttc aatgcacagg 180
ttgaaggcgg acgaagcgta tgttatcggg gaggagggcc agtatacacc tgtgggtgct 240
tacttggcaa tggacgagat catcgaaatt gcaaagaagc ataaggtgga tttcatccat 300
ccaggttatg ggttcttgtc tgaaaattcg gaatttgccg acaaagtagt gaaggccggt 360
atcacttgga tcggccctcc agctgaagtt attgactctg tgggtgacaa agtctctgcc 420
agacacttgg cagcaagagc taacgttcct accgttcccg gtactccagg acctatcgaa 480
actgtgcaag aggcacttga cttcgttaat gaatacggct acccggtgat cattaaggcc 540
gcctttggtg gtggtggtag aggtatgaga gtcgttagag aaggtgacga cgtggcagat 600
gcctttcaac gtgctacctc cgaagcccgt actgccttcg gtaatggtac ctgctttgtg 660
gaaagattct tggacaagcc aaagcatatt gaagttcaat tgttggctga taaccacgga 720
aacgtggttc atcttttcga aagagactgt tctgtgcaaa gaagacacca aaaagttgtc 780
gaagtcgctc cagcaaagac tttgccccgt gaagttcgtg acgctatttt gacagatgct 840
gttaaattag ctaaggtatg tggttacaga aacgcaggta ccgccgaatt cttggttgac 900
aaccaaaaca gacactattt cattgaaatt aatccaagaa ttcaagtgga gcataccatc 960
actgaagaaa tcaccggtat tgacattgtt tctgcccaaa tccagattgc cgcaggtgcc 1020
actttgactc aactaggtct attacaggat aaaatcacca cccgtgggtt ttccatccaa 1080
tgtcgtatta ccactgaaga tccctctaag aatttccaac cggataccgg tcgcctggag 1140
gtctatcgtt ctgccggtgg taatggtgtg agattggacg gtggtaacgc ttatgcaggt 1200
gctactatct cgcctcacta cgactcaatg ctggtcaaat gttcatgctc tggttctact 1260
tatgaaatcg tccgtaggaa gatgattcgt gccctgatcg aattcagaat cagaggtgtt 1320
aagaccaaca ttcccttcct attgactctt ttgaccaatc cagtttttat tgagggtaca 1380
tactggacga cttttattga cgacacccca caactgttcc aaatggtatc gtcacaaaac 1440
agagcgcaaa aactgttaca ctatttggca gacttggcag ttaacggttc ttctattaag 1500
ggtcaaattg gcttgccaaa actaaaatca aatccaagtg tcccccattt gcacgatgct 1560

-continued

```
caggg caatg tcatcaacgt tacaaagtct gcaccaccat ccggatggag acaagtgcta      1620
ctggaaaagg gaccatctga atttgccaag caagtcagac agttcaatgg tactctactg      1680
atggacacca cctggagaga cgctcatcaa tctctacttg caacaagagt cagaacccac      1740
gatttggcta caatcgctcc aacaaccgca catgcccttg caggtgcttt cgctttagaa      1800
tgttggggtg gtgctacatt cgacgttgca atgagattct tgcatgagga tccatgggaa      1860
cgtctgagaa aattaagatc tctggtgcct aatattccat tccaaatgtt attacgtggt      1920
gccaacggtg tggcttactc ttcattacct gacaatgcta ttgaccattt tgtcaagcaa      1980
gccaaggata atggtgttga tatatttaga gtttttgatg ccttgaatga tttagaacaa      2040
ttaaaagttg gtgtgaatgc tgtcaagaag gccggtggtg ttgtcgaagc tactgtttgt      2100
tactctggtg acatgcttca gccaggtaag aaatacaact tagactacta cctagaagtt      2160
gttgaaaaaa tagttcaaat gggtacacat atcttgggta ttaaggatat ggcaggtact      2220
atgaaaccgg ccgctgccaa attattaatt ggctccctaa gaaccagata tccggattta      2280
ccaattcatg ttcacagtca tgactccgca ggtactgctg ttgcgtctat gactgcatgt      2340
gccctagcag gtgctgatgt tgtcgatgta gctatcaatt caatgtcggg cttaacttcc      2400
caaccatcaa ttaatgcact gttggcttca ttagaaggta acattgatac tgggattaac      2460
gttgagcatg ttcgtgaatt agatgcatac tgggccgaaa tgagactgtt gtattcttgt      2520
ttcgaggccg acttgaaggg accagatcca gaagtttacc aacatgaaat cccaggtggt      2580
caattgacta acttgttatt ccaagctcaa caactgggtc ttggtgaaca atgggctgaa      2640
actaaaagag cttacagaga agccaattac ctactgggag atattgttaa agttacccca      2700
acttctaagg ttgtcggtga tttagctcaa ttcatggttt ctaacaaact gacttccgac      2760
gatattagac gtttagctaa ttcttttggac tttcctgact ctgttatgga cttttttgaa      2820
ggtttaattg gtcaaccata cggtgggttc ccagaaccat taagatctga tgtattgaga      2880
aacaagagaa gaaagttgac gtgccgtcca ggtttagaat tagaaccatt tgatctcgaa      2940
aaaattagag aagacttgca gaacagattc ggtgatattg atgaatgcga tgttgcttct      3000
tacaatatgt atccaagggt ctatgaagat ttccaaaaga tcagagaaac atacggtgat      3060
ttatcagttc taccaaccaa aaatttccta gcaccagcag aacctgatga agaaatcgaa      3120
gtcaccatcg aacaaggtaa gactttgatt atcaaattgc aagctgttgg tgacttaaat      3180
aagaaaactg ggcaaagaga agtgtatttt gaattgaacg tgaattaag aaagatcaga      3240 gttgcagaca agtcacaaaa catacaatct gttgctaaac caaaggctga tgtccacgat      3300
actcaccaaa tcggtgcacc aatggctggt gttatcatag aagttaaagt acataaaggg      3360
tctttggtga aaaagggcga atcgattgct gttttgagtg ccatgaaaat ggaaatggtt      3420
gtctcttcac cagcagatgg tcaagttaaa gacgttttca ttaaggatgg tgaaagtgtt      3480
gacgcatcag atttgttggt tgtcctagaa gaagaaaccc taccccatc ccaaaaaaag      3540 taa                                                                     3543
```

<210> SEQ ID NO 5
<211> LENGTH: 563
<212> TYPE: PRT
<213> ORGANISM: Saccharomyces cerevisiae

<400> SEQUENCE: 5

```
Met Ser Glu Ile Thr Leu Gly Lys Tyr Leu Phe Glu Arg Leu Lys Gln
 1               5                  10                  15
```

```
Val Asn Val Asn Thr Val Phe Gly Leu Pro Gly Asp Phe Asn Leu Ser
             20                  25                  30

Leu Leu Asp Lys Ile Tyr Glu Val Glu Gly Met Arg Trp Ala Gly Asn
         35                  40                  45

Ala Asn Glu Leu Asn Ala Ala Tyr Ala Ala Asp Gly Tyr Ala Arg Ile
     50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ala Gln Ala Lys Gln Leu Leu
                100                 105                 110

Leu His His Thr Leu Gly Asn Gly Asp Phe Thr Val Phe His Arg Met
             115                 120                 125

Ser Ala Asn Ile Ser Glu Thr Thr Ala Met Ile Thr Asp Ile Ala Thr
130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
                180                 185                 190

Asp Ala Glu Ser Glu Lys Glu Val Ile Asp Thr Ile Leu Ala Leu Val
             195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
                260                 265                 270

Lys Glu Ala Val Glu Ser Ala Asp Leu Ile Leu Ser Val Gly Ala Leu
             275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
             355                 360                 365

Trp Met Trp Asn Gln Leu Gly Asn Phe Leu Gln Glu Gly Asp Val Val
         370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430
```

-continued

```
Asp Pro Lys Lys Arg Val Ile Leu Phe Ile Gly Asp Gly Ser Leu Gln
             435                 440                 445

Leu Thr Val Gln Glu Ile Ser Thr Met Ile Arg Trp Gly Leu Lys Pro
        450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 6
<211> LENGTH: 1692
<212> TYPE: DNA
<213> ORGANISM: Saccharomyces cerevisiae

<400> SEQUENCE: 6
atgtctgaaa ttactttggg taaatatttg ttcgaaagat aaagcaagt caacgttaac      60
accgttttcg gtttgccagg tgacttcaac ttgtccttgt ggacaagat ctacgaagtt     120
gaaggtatga gatgggctgg taacgccaac gaattgaacg ctgcttacgc cgctgatggt    180
tacgctcgta tcaagggtat gtcttgtatc atcaccacct tcggtgtcgg tgaattgtct    240
gctttgaacg gtattgccgg ttcttacgct gaaacgtcg gtgttttgca cgttgttggt    300
gtcccatcca tctctgctca agctaagcaa ttgttgttgc accacacctt gggtaacggt    360
gacttcactg tttccacag aatgtctgcc aacatttctg aaaccactgc tatgatcact    420
gacattgcta ccgccccagc tgaaattgac agatgtatca gaaccactta cgtcacccaa    480
agaccagtct acttaggttt gccagctaac ttggtcgact tgaacgtccc agctaagttg    540
ttgcaaactc caattgacat gtcttttgaag ccaaacgatg ctgaatccga aaaggaagtc    600
attgacacca tcttggcttt ggtcaaggat gctaagaacc cagttatctt ggctgatgct    660
tgttgttcca gacacgacgt caaggctgaa actaagaagt tgattgactt gactcaattc    720
ccagctttcg tcaccccaat gggtaagggt tccattgacg aacaacaccc aagatacggt    780
ggtgtttacg tcggtacctt gtccaagcca gaagttaagg aagccgttga atctgctgac    840
ttgattttgt ctgtcggtgc tttgttgtct gatttcaaca ccggttcttt ctcttactct    900
tacaagacca gaacattgt cgaattccac tccgaccaca tgaagatcag aaacgccact    960
ttcccaggtg tccaaatgaa attcgttttg caaaagttgt tgaccactat tgctgacgcc   1020
gctaagggtt acaagccagt tgctgtccca gctagaactc cagctaacgc tgctgtccca   1080
gcttctaccc cattgaagca agaatggatg tggaaccaat gggtaacttc ttgcaagaa    1140
ggtgatgttg tcattgctga aaccggtacc tccgctttcg gtatcaacca aaccactttc   1200
ccaaacaaca cctacggtat ctctcaagtc ttatggggtt ccattggttt caccactggt   1260
gctaccttgg gtgctgcttt cgctgctgaa gaaattgatc aaagaagag agttatctta   1320
ttcattggtg acggttcttt gcaattgact gttcaagaaa tctccaccat gatcagatgg   1380
```

-continued

```
ggcttgaagc catacttgtt cgtcttgaac aacgatggtt acaccattga aaagttgatt    1440
cacggtccaa aggctcaata caacgaaatt caaggttggg accacctatc cttgttgcca    1500
actttcggtg ctaaggacta tgaaacccac agagtcgcta ccaccggtga atgggacaag    1560
ttgacccaag acaagtcttt caacgacaac tctaagatca gaatgattga atcatgttg     1620 ccagtcttcg atgctccaca aaacttggtt gaacaagcta agttgactgc tgctaccaac    1680
gctaagcaat aa                                                        1692
```

<210> SEQ ID NO 7
<211> LENGTH: 591
<212> TYPE: PRT
<213> ORGANISM: Saccharomyces cerevisiae

<400> SEQUENCE: 7

```
Met Leu Lys Tyr Lys Pro Leu Leu Lys Ile Ser Lys Asn Cys Glu Ala
 1               5                  10                  15

Ala Ile Leu Arg Ala Ser Lys Thr Arg Leu Asn Thr Ile Arg Ala Tyr
             20                  25                  30

Gly Ser Thr Val Pro Lys Ser Lys Ser Phe Glu Gln Asp Ser Arg Lys
         35                  40                  45

Arg Thr Gln Ser Trp Thr Ala Leu Arg Val Gly Ala Ile Leu Ala Ala
     50                  55                  60

Thr Ser Ser Val Ala Tyr Leu Asn Trp His Asn Gly Gln Ile Asp Asn
 65                  70                  75                  80

Glu Pro Lys Leu Asp Met Asn Lys Gln Lys Ile Ser Pro Ala Glu Val
                 85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
```

```
                305                 310                 315                 320
Ala Ala Pro Ser Asp Lys Gln Ile Gln Trp Tyr Gln Leu Tyr Val Asn
                    325                 330                 335

Ser Asp Arg Lys Ile Thr Asp Asp Leu Val Lys Asn Val Glu Lys Leu
                    340                 345                 350

Gly Val Lys Ala Leu Phe Val Thr Val Asp Ala Pro Ser Leu Gly Gln
                    355                 360                 365

Arg Glu Lys Asp Met Lys Leu Lys Phe Ser Asn Thr Lys Ala Gly Pro
                    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                    405                 410                 415

Glu Leu Lys Lys Lys Thr Lys Leu Pro Ile Val Ile Lys Gly Val Gln
                    420                 425                 430

Arg Thr Glu Asp Val Ile Lys Ala Ala Glu Ile Gly Val Ser Gly Val
                    435                 440                 445

Val Leu Ser Asn His Gly Gly Arg Gln Leu Asp Phe Ser Arg Ala Pro
450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                    485                 490                 495

Asp Val Leu Lys Ala Leu Cys Leu Gly Ala Lys Gly Val Gly Leu Gly
                    500                 505                 510

Arg Pro Phe Leu Tyr Ala Asn Ser Cys Tyr Gly Arg Asn Gly Val Glu
                    515                 520                 525

Lys Ala Ile Glu Ile Leu Arg Asp Glu Ile Glu Met Ser Met Arg Leu
                    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                    565                 570                 575

Asn Glu Val Tyr Glu Gly Pro Thr Leu Thr Glu Phe Glu Asp Ala
                    580                 585                 590

<210> SEQ ID NO 8
<211> LENGTH: 1776
<212> TYPE: DNA
<213> ORGANISM: Saccharomyces cerevisiae

<400> SEQUENCE: 8
atgctaaaat acaaaccttt actaaaaatc tcgaagaact gtgaggctgc tatcctcaga        60
gcgtctaaga ctagattgaa cacaatccgc gcgtacggtt ctaccgttcc aaaatccaag       120
tcgttcgaac aagactcaag aaaacgcaca cagtcatgga ctgccttgag agtcggtgca       180
attctagccg ctactagttc cgtggcgtat ctaaactggc ataatggcca aatagacaac       240
gagccgaaac tggatatgaa taaacaaaag atttcgcccg ctgaagttgc caagcataac       300
aagcccgatg attgttgggt tgtgatcaat ggttacgtat acgacttaac gcgattccta       360
ccaaatcatc caggtgggca ggatgttatc aagtttaacg ccgggaaaga tgtcactgct       420 attttgaac cactacatgc tcctaatgtc atcgataagt atatagctcc cgagaaaaaa       480
ttgggtcccc ttcaaggatc catgcctcct gaacttgtct gtcctcctta tgctcctggt       540
```

```
gaaactaagg aagatatcgc tagaaaagaa caactaaaat cgctgctacc tcctctagat   600
aatattatta acctttacga ctttgaatac ttggcctctc aaactttgac taaacaagcg   660
tgggcctact attcctccgg tgctaacgac gaagttactc acagagaaaa ccataatgct   720
tatcatagga tttttttcaa accaaagatc cttgtagatg tacgcaaagt agacatttca   780
actgacatgt tgggttctca tgtggatgtt cccttctacg tgtctgctac agctttgtgt   840
aaactgggaa accccttaga aggtgaaaaa gatgtcgcca gaggttgtgg ccaaggtgtg   900
acaaaagtcc cacaaatgat atctactttg gcttcatgtt ccctgagga aattattgaa    960 gcagcaccct ctgataaaca aattcaatgg taccaactat atgttaactc tgatagaaag  1020
atcactgatg atttggttaa aaatgtagaa aagctgggtg taaaggcatt atttgtcact  1080
gtggatgctc caagtttagg tcaaagagaa aaagatatga agctgaaatt ttccaataca  1140
aaggctggtc caaaagcgat gaagaaaact aatgtagaag aatctcaagg tgcttcgaga  1200
gcgttatcaa agtttattga cccctctttg acttggaaag atatagaaga gttgaagaaa  1260
aagacaaaac tacctattgt tatcaaaggt gttcaacgta ccgaagatgt tatcaaagca  1320
gcagaaatcg gtgtaagtgg ggtggttcta tccaatcatg gtggtagaca attagatttt  1380
tcaagggctc ccattgaagt cctggctgaa accatgccaa tcctggaaca acgtaacttg  1440
aaggataagt tggaagtttt cgtggacggt ggtgttcgtc gtggtacaga tgtcttgaaa  1500
gcgttatgtc taggtgctaa aggtgttggt ttgggtagac cattcttgta tgcgaactca  1560
tgctatggtc gtaatggtgt tgaaaaagcc attgaaattt taagagatga aattgaaatg  1620
tctatgagac tattaggtgt tactagcatt gcggaattga gcctgatct tttagatcta  1680 tcaacactaa aggcaagaac agttggagta ccaaacgacg tgctgtataa tgaagtttat  1740
gagggaccta ctttaacaga atttgaggat gcatga                            1776
```

<210> SEQ ID NO 9
<211> LENGTH: 391
<212> TYPE: PRT
<213> ORGANISM: Saccharomyces cerevisiae

<400> SEQUENCE: 9

```
Met Ser Ala Ala Ala Asp Arg Leu Asn Leu Thr Ser Gly His Leu Asn
  1               5                  10                  15

Ala Gly Arg Lys Arg Ser Ser Ser Val Ser Leu Lys Ala Ala Glu
             20                  25                  30

Lys Pro Phe Lys Val Thr Val Ile Gly Ser Gly Asn Trp Gly Thr Thr
         35                  40                  45

Ile Ala Lys Val Val Ala Glu Asn Cys Lys Gly Tyr Pro Glu Val Phe
     50                  55                  60

Ala Pro Ile Val Gln Met Trp Val Phe Glu Glu Ile Asn Gly Glu
 65                  70                  75                  80

Lys Leu Thr Glu Ile Ile Asn Thr Arg His Gln Asn Val Lys Tyr Leu
                 85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160
```

Val Gln Leu Leu Ser Ser Tyr Ile Thr Glu Glu Leu Gly Ile Gln Cys
            165                 170                 175

Gly Ala Leu Ser Gly Ala Asn Ile Ala Thr Glu Val Ala Gln Glu His
        180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
        210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 10
<211> LENGTH: 1176
<212> TYPE: DNA
<213> ORGANISM: Saccharomyces cerevisiae

<400> SEQUENCE: 10
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact      300 ctacccgaca atttggttgc taatccagac ttgattgatt cagtcaagga tgtcgacatc     360
atcgttttca acattccaca tcaattttg ccccgtatct gtagccaatt gaaaggtcat      420
gttgattcac acgtcagagc tatctcctgt ctaaagggtt tgaagttgg tgctaaaggt      480 gtccaattgc tatcctctta catcactgag gaactaggta ttcaatgtgg tgctctatct     540
ggtgctaaca ttgccaccga agtcgctcaa gaacactggt ctgaaacaac agttgcttac     600
cacattccaa aggatttcag aggcgagggc aaggacgtcg accataaggt tctaaaggcc     660
ttgttccaca gacctactt ccacgttagt gtcatcgaag atgttgctgg tatctccatc      720
tgtggtgctt tgaagaacgt tgttgcctta ggttgtggtt tcgtcgaagg tctaggctgg     780

```
ggtaacaacg cttctgctgc catccaaaga gtcggtttgg gtgagatcat cagattcggt    840
caaatgtttt tcccagaatc tagagaagaa acatactacc aagagtctgc tggtgttgct    900
gatttgatca ccacctgcgc tggtggtaga aacgtcaagg ttgctaggct aatggctact    960
tctggtaagg acgcctggga atgtgaaaag gagttgttga atggccaatc cgctcaaggt   1020
ttaattacct gcaaagaagt tcacgaatgg ttggaaacat gtggctctgt cgaagacttc   1080
ccattatttg aagccgtata ccaaatcgtt tacaacaact acccaatgaa gaacctgccg   1140
gacatgattg aagaattaga tctacatgaa gattag                            1176
```

<210> SEQ ID NO 11
<211> LENGTH: 560
<212> TYPE: PRT
<213> ORGANISM: Saccharomyces cerevisiae

<400> SEQUENCE: 11

```
Met Ile Arg Gln Ser Leu Met Lys Thr Val Trp Ala Asn Ser Ser Arg
  1               5                  10                  15

Phe Ser Leu Gln Ser Lys Ser Gly Leu Val Lys Tyr Ala Lys Asn Arg
             20                  25                  30

Ser Phe His Ala Ala Arg Asn Leu Leu Glu Asp Lys Lys Val Ile Leu
         35                  40                  45

Gln Lys Val Ala Pro Thr Thr Gly Val Ala Lys Gln Ser Phe Phe
     50                  55                  60

Lys Arg Thr Gly Lys Phe Thr Leu Lys Ala Leu Leu Tyr Ser Ala Leu
 65                  70                  75                  80

Ala Gly Thr Ala Tyr Val Ser Tyr Ser Leu Tyr Arg Glu Ala Asn Pro
                 85                  90                  95

Ser Thr Gln Val Pro Gln Ser Asp Thr Phe Pro Asn Gly Ser Lys Arg
            100                 105                 110

Lys Thr Leu Val Ile Leu Gly Ser Gly Trp Gly Ser Val Ser Leu Leu
        115                 120                 125

Lys Asn Leu Asp Thr Thr Leu Tyr Asn Val Val Val Ser Pro Arg
    130                 135                 140

Asn Tyr Phe Leu Phe Thr Pro Leu Leu Pro Ser Thr Pro Val Gly Thr
145                 150                 155                 160

Ile Glu Leu Lys Ser Ile Val Glu Pro Val Arg Thr Ile Ala Arg Arg
                165                 170                 175

Ser His Gly Glu Val His Tyr Tyr Glu Ala Glu Ala Tyr Asp Val Asp
            180                 185                 190

Pro Glu Asn Lys Thr Ile Lys Val Lys Ser Ser Ala Lys Asn Asn Asp
        195                 200                 205

Tyr Asp Leu Asp Leu Lys Tyr Asp Tyr Leu Val Gly Val Gly Ala
    210                 215                 220

Gln Pro Asn Thr Phe Gly Thr Pro Gly Val Tyr Glu Tyr Ser Ser Phe
225                 230                 235                 240

Leu Lys Glu Ile Ser Asp Ala Gln Glu Ile Arg Leu Lys Ile Met Ser
                245                 250                 255

Ser Ile Glu Lys Ala Ala Ser Leu Ser Pro Lys Asp Pro Glu Arg Ala
            260                 265                 270

Arg Leu Leu Ser Phe Val Val Gly Gly Gly Pro Thr Gly Val Glu
        275                 280                 285

Phe Ala Ala Glu Leu Arg Asp Tyr Val Asp Gln Asp Leu Arg Lys Trp
    290                 295                 300
```

```
Met Pro Glu Leu Ser Lys Glu Ile Lys Val Thr Leu Val Glu Ala Leu
305                 310                 315                 320

Pro Asn Ile Leu Asn Met Phe Asp Lys Tyr Leu Val Asp Tyr Ala Gln
            325                 330                 335

Asp Leu Phe Lys Glu Glu Lys Ile Asp Leu Arg Leu Lys Thr Met Val
        340                 345                 350

Lys Lys Val Asp Ala Thr Thr Ile Thr Ala Lys Thr Gly Asp Gly Asp
    355                 360                 365

Ile Glu Asn Ile Pro Tyr Gly Val Leu Val Trp Ala Thr Gly Asn Ala
370                 375                 380

Pro Arg Glu Val Ser Lys Asn Leu Met Thr Lys Leu Glu Glu Gln Asp
385                 390                 395                 400

Ser Arg Arg Gly Leu Leu Ile Asp Asn Lys Leu Gln Leu Leu Gly Ala
                405                 410                 415

Lys Gly Ser Ile Phe Ala Ile Gly Asp Cys Thr Phe His Pro Gly Leu
            420                 425                 430

Phe Pro Thr Ala Gln Val Ala His Gln Glu Gly Glu Tyr Leu Ala Gln
        435                 440                 445

Tyr Phe Lys Lys Ala Tyr Lys Ile Asp Gln Leu Asn Trp Lys Met Thr
    450                 455                 460

His Ala Lys Asp Asp Ser Glu Val Ala Arg Leu Lys Asn Gln Ile Val
465                 470                 475                 480

Lys Thr Gln Ser Gln Ile Glu Asp Phe Lys Tyr Asn His Lys Gly Ala
                485                 490                 495

Leu Ala Tyr Ile Gly Ser Asp Lys Ala Ile Ala Asp Leu Ala Val Gly
            500                 505                 510

Glu Ala Lys Tyr Arg Leu Ala Gly Ser Phe Thr Phe Leu Phe Trp Lys
        515                 520                 525

Ser Ala Tyr Leu Ala Met Cys Leu Ser Phe Arg Asn Arg Val Leu Val
    530                 535                 540

Ala Met Asp Trp Ala Lys Val Tyr Phe Leu Gly Arg Asp Ser Ser Ile
545                 550                 555                 560

<210> SEQ ID NO 12
<211> LENGTH: 545
<212> TYPE: PRT
<213> ORGANISM: Saccharomyces cerevisiae

<400> SEQUENCE: 12

Met Leu Pro Arg Leu Gly Phe Ala Arg Thr Ala Arg Ser Ile His Arg
1               5                   10                  15

Phe Lys Met Thr Gln Ile Ser Lys Pro Phe His Ser Thr Glu Val
            20                  25                  30

Gly Lys Pro Gly Pro Gln Gln Lys Leu Ser Lys Ser Tyr Thr Ala Val
        35                  40                  45

Phe Lys Lys Trp Phe Val Arg Gly Leu Lys Leu Thr Phe Tyr Thr Thr
    50                  55                  60

Leu Ala Gly Thr Leu Tyr Val Ser Tyr Glu Leu Tyr Lys Glu Ser Asn
65                  70                  75                  80

Pro Pro Lys Gln Val Pro Gln Ser Thr Ala Phe Ala Asn Gly Leu Lys
                85                  90                  95

Lys Lys Glu Leu Val Ile Leu Gly Thr Gly Trp Gly Ala Ile Ser Leu
            100                 105                 110

Leu Lys Lys Leu Asp Thr Ser Leu Tyr Asn Val Thr Val Val Ser Pro
```

```
            115                 120                 125
Arg Ser Phe Phe Leu Phe Thr Pro Leu Leu Pro Ser Thr Pro Val Gly
    130                 135                 140

Thr Ile Glu Met Lys Ser Ile Val Glu Pro Val Arg Ser Ile Ala Arg
145                 150                 155                 160

Arg Thr Pro Gly Glu Val His Tyr Ile Glu Ala Glu Ala Leu Asp Val
                165                 170                 175

Asp Pro Lys Ala Lys Lys Val Met Val Gln Ser Val Ser Glu Asp Glu
            180                 185                 190

Tyr Phe Val Ser Ser Leu Ser Tyr Asp Tyr Leu Val Val Ser Val Gly
        195                 200                 205

Ala Lys Thr Thr Thr Phe Asn Ile Pro Gly Val Tyr Gly Asn Ala Asn
    210                 215                 220

Phe Leu Lys Glu Ile Glu Asp Ala Gln Asn Ile Arg Met Lys Leu Met
225                 230                 235                 240

Lys Thr Ile Glu Gln Ala Ser Ser Phe Pro Val Asn Asp Pro Glu Arg
                245                 250                 255

Lys Arg Leu Leu Thr Phe Val Val Gly Gly Pro Thr Gly Val
            260                 265                 270

Glu Phe Ala Ala Glu Leu Gln Asp Tyr Ile Asn Gln Asp Leu Arg Lys
        275                 280                 285

Trp Met Pro Asp Leu Ser Lys Glu Met Lys Val Ile Leu Ile Glu Ala
    290                 295                 300

Leu Pro Asn Ile Leu Asn Met Phe Asp Lys Thr Leu Ile Lys Tyr Ala
305                 310                 315                 320

Glu Asp Leu Phe Ala Arg Asp Glu Ile Asp Leu Gln Val Asn Thr Ala
                325                 330                 335

Val Lys Val Val Glu Pro Thr Tyr Ile Arg Thr Leu Gln Asn Gly Gln
            340                 345                 350

Thr Asn Thr Asp Ile Glu Tyr Gly Met Leu Val Trp Ala Thr Gly Asn
        355                 360                 365

Glu Pro Ile Asp Phe Ser Lys Thr Leu Met Ser Arg Ile Pro Glu Gln
    370                 375                 380

Thr Asn Arg Arg Gly Leu Leu Ile Asn Asp Lys Leu Glu Leu Leu Gly
385                 390                 395                 400

Ser Glu Asn Ser Ile Tyr Ala Ile Gly Asp Cys Thr Ala His Thr Gly
                405                 410                 415

Phe Phe Pro Thr Ala Gln Val Ala His Gln Glu Gly Glu Tyr Leu Ala
            420                 425                 430

Lys Ile Leu Asp Lys Lys Leu Gln Ile Glu Gln Leu Glu Trp Asp Met
        435                 440                 445

Leu Asn Ser Thr Asp Glu Thr Glu Val Ser Arg Leu Gln Lys Glu Val
    450                 455                 460

Asn Leu Arg Lys Ser Lys Leu Asp Lys Phe Asn Tyr Lys His Met Gly
465                 470                 475                 480

Ala Leu Ala Tyr Ile Gly Ser Glu Thr Ala Ile Ala Asp Leu His Met
                485                 490                 495

Gly Asp Ser Ser Tyr Gln Leu Lys Gly Met Phe Ala Phe Leu Phe Trp
            500                 505                 510

Lys Ser Ala Tyr Leu Ala Met Cys Leu Ser Ile Arg Asn Arg Ile Leu
        515                 520                 525

Ile Ala Met Asp Trp Thr Lys Val Tyr Phe Leu Gly Arg Asp Ser Ser
    530                 535                 540
```

Val
545

<210> SEQ ID NO 13
<211> LENGTH: 1683
<212> TYPE: DNA
<213> ORGANISM: Saccharomyces cerevisiae

<400> SEQUENCE: 13

```
atgattagac aatcattaat gaaaacagtg tgggctaact cctccaggtt tagcctacag      60
agcaagtcgg ggcttgtgaa atatgccaaa aatagatcgt tccatgcagc aagaaatttg     120
ctagaggaca agaaagtcat tttgcaaaaa gtggcgccca ctactggcgt tgttgcgaag     180
cagtcctttt tcaagagaac tgggaaattt actttgaagg cttta ttgta ttctgccctc    240
gcgggtacgg cttacgtttc atactcactt taccgagaag ctaacccttc tacccaagtt    300
cctcaatcgg acacttttcc aaacggttca agaggaaga cttt ggtaat tctgggctcc    360
ggttggggtt ctgtgtcgct tttgaaaaat ttggacacca cgttgtataa tgttgttgtt    420
gtttctccaa gaaattattt tcttttttact ccgctattgc catctacccc agttggtacc    480
atcgaattga aatctattgt tgaacctgtc aggactattg ctagaagatc gcacggtgaa    540
gtccattact atgaagctga agcgtacgac gttgatcctg aaaacaaaac aattaaggtc    600
aaatcttccg ctaagaataa cgactacgac ttggacttga aatacgacta tctggttgtc    660
ggtgtgggtg ctcaaccaaa cacttttggt actccgggag tttatgaata ttcttctttc    720
ttgaaggaaa tatccgacgc tcaagagatc agattaaaaa ttatgtccag tattgagaaa    780
gctgcctccc tatctccaaa agatcctgag agagcaagat tgttgagctt tgttgtcgtt    840
ggtggtggtc ccaccggtgt cgaatttgcc gctgaattga gagattatgt tgaccaggac    900
ttgagaaaat ggatgcccga attgagtaaa gaaattaaag tcactttggt ggaggctttg    960
ccaaacattt tgaacatgtt tgacaagtat ctcgttgact atgctcaaga tttattcaaa   1020
gaggaaaaaa tcgatttaag attgaaaaca atggttaaga agttgacgc taccactata   1080
actgccaaaa ctggcgatgg tgacattgaa aatataccgt atggtgtatt agtttgggct   1140
acaggtaatg cgccaagaga agtgtctaag aacctaatga ctaaattaga ggaacaggac   1200
tcaagacgtg gtttgttgat agataacaaa cttcaacttt tgggtgctaa gggatctatt   1260
tttgctatcg gcgattgtac cttccaccct ggcttgttcc ctaccgctca agttgcccac   1320
caagaaggtg aatacttggc tcagtatttc aagaaagctt ataaaatcga tcaattgaac   1380
tggaaaatga cccatgctaa agacgattca gaagtcgcta gattaaagaa ccaaatagtc   1440
aaaacgcaat cgcaaattga agacttcaag tacaaccata agggtgctct ggcttatatt   1500
ggttcagata aagccattgc tgatcttgcc gttggtgaag ccaaatatag gttagccggc   1560
tcattcacct tcctattctg gaaatctgct tatttggcaa tgtgtctatc ctttagaaac   1620
agagttcttg tcgctatgga ttgggctaaa gtttatttct gggtagaga ttcatctatc   1680
tag                                                                 1683
```

<210> SEQ ID NO 14
<211> LENGTH: 1638
<212> TYPE: DNA
<213> ORGANISM: Saccharomyces cerevisiae

<400> SEQUENCE: 14

```
atgctgccca gacttggttt tgcgaggact gctaggtcca tacaccgttt caagatgacc       60
```

```
cagatctcta aacctttttt ccattccact gaagttggta agcccggacc acagcagaag    120
ctatcgaaat cttacactgc ggtattcaag aaatggtttg tcagaggttt aaagttaacc    180
ttttacacga cgttggccgg cacattgtat gtgtcatacg agctgtacaa agaatcgaac    240
ccacccaaac aggttcccca atcgaccgct tttgctaatg gtttgaaaaa gaaggagctg    300
gttattttgg gtacaggctg gggcgccata tctcttttga agaaattaga cacgtctttg    360
tataacgtga ccgtggtgtc gccaagaagc ttcttttgt tcacaccgtt attccctca     420 acgcctgtgg gtacgataga gatgaagtct attgtcgaac cggttagatc gatcgctaga    480
agaacgcctg gagaagttca ctacattgag gcggaagcgt tggacgttga tccaaaggcc    540
aaaaaagtaa tggtgcaatc ggtgtcagag gacgaatatt tcgtttcgag cttaagttac    600
gattatcttg ttgttagtgt aggcgctaaa accactactt ttaacattcc cggggtctat    660
ggcaatgcta acttcttgaa agagattgaa gatgctcaaa atattcgtat gaagttaatg    720
aaaaccatag aacaggcaag ttcatttcct gtgaacgatc cggaaaggaa gcgattatta    780
acgttcgtgg ttgttggagg gggccctacg ggggttgaat ttgccgccga actgcaagat    840
tacatcaatc aagatttgag gaagtggatg cccgacttaa gtaaagaaat gaaggttatc    900
ttaattgaag ccctgcctaa tatcctaaac atgttcgata agacgttgat caagtatgcc    960
gaggaccttt tgccagaga tgaaattgac ttgcaagtga atactgccgt gaaagtcgta   1020
gagccaacct atatacgcac tctgcaaaac ggccaaacaa acacggatat cgaatacggg   1080
atgctggttt gggccacggg aaatgaacca atcgattttt caaagacact gatgagtaga   1140
ataccggagc aaactaatag gcgtggtctg ttaattaatg acaagttgga gcttctcggt   1200
tctgagaatt cgatttatgc aattggtgat tgtaccgcac acacgggttt ctttcccacg   1260
gcacaagttg cacatcagga aggcgaatac ttggccaaga tcttggataa aaaattacag   1320
atagaacaat tggaatggga catgctcaac agtaccgatg aaactgaggt atcacgtcta   1380
caaaaagagg ttaatttgag gaaatctaag ttggataagt tcaactacaa gcatatgggt   1440
gcccttgcgt acatcggctc tgaaaccgca attgcagatt tgcatatggg cgactcatca   1500
taccagttga aaggtatgtt tgccttcttg ttttggaaat ccgcttattt ggccatgtgt   1560
ctctctatca ggaataggat tttaattgcc atggactgga ccaaagttta ctttcttgga   1620
agggattcct ccgtgtag                                                 1638
```

<210> SEQ ID NO 15
<211> LENGTH: 332
<212> TYPE: PRT
<213> ORGANISM: Pelodiscus sinensis japonicus

<400> SEQUENCE: 15

Met Ser Val Lys Glu Leu Leu Ile Gln Asn Val His Lys Glu Glu His
1               5                   10                  15

Ser His Ala His Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Arg Gly Glu Met Leu Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala His Ser Lys Leu Val Ile Ile Thr Ala

```
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
                325                 330

<210> SEQ ID NO 16
<211> LENGTH: 332
<212> TYPE: PRT
<213> ORGANISM: Ornithorhynchus anatinus

<400> SEQUENCE: 16

Met Ala Gly Val Lys Glu Gln Leu Ile Gln Asn Leu Leu Lys Glu Glu
 1               5                  10                  15

Tyr Ala Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125
```

```
Pro Asn Cys Lys Leu Leu Val Val Ser Asn Pro Val Asp Ile Leu Thr
    130                 135                 140
Tyr Val Ala Trp Lys Ile Ser Gly Phe Pro Lys Asn Arg Val Ile Gly
145                 150                 155                 160
Ser Gly Cys Asn Leu Asp Ser Ala Arg Phe Arg Tyr Leu Met Gly Glu
                165                 170                 175
Arg Leu Gly Ile His Ser Thr Ser Cys His Gly Trp Val Ile Gly Glu
            180                 185                 190
His Gly Asp Ser Ser Val Pro Val Trp Ser Gly Val Asn Val Ala Gly
        195                 200                 205
Val Ser Leu Lys Asn Leu His Pro Asp Leu Gly Thr Asp Ala Asp Lys
210                 215                 220
Glu Gln Trp Lys Asp Val His Lys Gln Val Val Asp Ser Ala Tyr Glu
225                 230                 235                 240
Val Ile Lys Leu Lys Gly Tyr Thr Ser Trp Ala Ile Gly Leu Ser Val
                245                 250                 255
Ala Asp Leu Ala Glu Ser Ile Val Lys Asn Leu Arg Arg Val His Pro
                260                 265                 270
Ile Ser Thr Met Ile Lys Gly Leu Tyr Gly Ile Lys Asp Glu Val Phe
            275                 280                 285
Leu Ser Val Pro Cys Val Leu Gly Gln Asn Gly Ile Ser Asp Val Val
        290                 295                 300
Lys Ile Thr Leu Lys Ser Glu Glu Glu Ala His Leu Lys Lys Ser Ala
305                 310                 315                 320
Asp Thr Leu Trp Gly Ile Gln Lys Glu Leu Gln Phe
                325                 330

<210> SEQ ID NO 17
<211> LENGTH: 332
<212> TYPE: PRT
<213> ORGANISM: Tursiops truncatus

<400> SEQUENCE: 17

Met Ala Thr Val Lys Asp Gln Leu Ile Gln Asn Leu Leu Lys Glu Glu
  1               5                  10                  15
His Val Pro Gln Asn Lys Ile Thr Val Val Gly Val Gly Ala Val Gly
                20                  25                  30
Met Ala Cys Ala Ile Ser Ile Leu Met Lys Asp Leu Ala Asp Glu Leu
            35                  40                  45
Ala Leu Val Asp Val Ile Glu Asp Lys Leu Lys Gly Glu Met Met Asp
        50                  55                  60
Leu Gln His Gly Ser Leu Phe Leu Arg Thr Pro Lys Ile Val Ser Gly
65                  70                  75                  80
Lys Asp Tyr Ser Val Thr Ala Asn Ser Lys Leu Val Ile Ile Thr Ala
                85                  90                  95
Gly Ala Arg Gln Gln Glu Gly Glu Ser Arg Leu Asn Leu Val Gln Arg
            100                 105                 110
Asn Val Asn Ile Phe Lys Phe Ile Val Pro Asn Ile Val Lys Tyr Ser
        115                 120                 125
Pro His Cys Lys Leu Leu Val Ser Asn Pro Val Asp Ile Leu Thr
    130                 135                 140
Tyr Val Ala Trp Lys Ile Ser Gly Phe Pro Lys Asn Arg Val Ile Gly
145                 150                 155                 160
Ser Gly Cys Asn Leu Asp Ser Ala Arg Phe Arg Tyr Leu Met Gly Glu
                165                 170                 175
```

```
Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330

<210> SEQ ID NO 18
<211> LENGTH: 332
<212> TYPE: PRT
<213> ORGANISM: Rattus norvegicus

<400> SEQUENCE: 18

Met Ala Ala Leu Lys Asp Gln Leu Ile Val Asn Leu Leu Lys Glu Glu
1               5                   10                  15

Gln Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Gln Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
        195                 200                 205

Val Ser Leu Lys Ser Leu Asn Pro Gln Leu Gly Thr Asp Ala Asp Lys
    210                 215                 220
```

```
              210              215              220
Glu Gln Trp Lys Asp Val His Lys Gln Val Val Asp Ser Ala Tyr Glu
225              230              235              240

Val Ile Lys Leu Lys Gly Tyr Thr Ser Trp Ala Ile Gly Leu Ser Val
                245              250              255

Ala Asp Leu Ala Glu Ser Ile Met Lys Asn Leu Arg Arg Val His Pro
            260              265              270

Ile Ser Thr Met Ile Lys Gly Leu Tyr Gly Ile Lys Glu Asp Val Phe
        275              280              285

Leu Ser Val Pro Cys Ile Leu Gly Gln Asn Gly Ile Ser Asp Val Val
    290              295              300

Lys Val Thr Leu Thr Pro Asp Glu Glu Ala Arg Leu Lys Lys Ser Ala
305              310              315              320

Asp Thr Leu Trp Gly Ile Gln Lys Glu Leu Gln Phe
                325              330

<210> SEQ ID NO 19
<211> LENGTH: 999
<212> TYPE: DNA
<213> ORGANISM: Pelodiscus sinensis japonicus

<400> SEQUENCE: 19
atgtccgtaa aggaactact tatacaaaac gtccataagg aggagcattc tcacgctcac    60
aataagataa cagttgtagg agtaggtgca gtaggtatgg catgtgctat ttcgatatta   120
atgaaagact tggctgatga actagccttg gttgatgtga ttgaggataa gttacgtgga   180
gaaatgttag atttgcaaca tggttcattg ttcttgagaa cccccaaaat tgtctcgggt   240
aaggattatt cagtcactgc tcattctaaa ctggttatca ttacagcagg tgcaagacag   300
caagaagggg agagcagact aaatctggtt caacgtaatg tcaacatctt caagtttatc   360
atcccgaacg tagtaaaata cagtccagac tgcatgttgc ttgttgtgag taatccagtt   420
gacatcttaa cctatgttgc gtggaaaatc agtgggtttc caaaacatag ggtgattggc   480
tcaggatgca accttgatag cgccaggttt aggtatctaa tgggagaaaa attaggtatt   540
cactccttat cttgtcatgg ctggataata ggcgaacatg tgattcttc ggtacctgtt   600 tggtccgggg ttaatgtggc tggtgttagt ttaaaagcat tatatcctga cctgggtact   660
gatgccgata agaacattg gaaagaagtg cacaaacaag tggttgattc tgcttacgaa   720
gttattaaac ttaagggcta cacttcttgg gctataggtc tatcagtagc tgatttggca   780
gaaaccgtta tgaaaaattt aagaagagtc cacccaattt ccacgatggt caagggtatg   840
tacggtgtta gctctgacgt cttcttatct gttccttgtg ttttgggata tgcgggaatt   900
acagacgtcg tgaagatgac attgaaatca gaggaagagg aaaaactaag aaagtcagcc   960
gatactctgt ggggcattca aaaggaattg cagttttaa                          999

<210> SEQ ID NO 20
<211> LENGTH: 1267
<212> TYPE: DNA
<213> ORGANISM: Artificial Sequence
<220> FEATURE:
<223> OTHER INFORMATION: Synthetic (ARS/CEN)

<400> SEQUENCE: 20
gagctccttt catttctgat aaaagtaaga ttactccatt tatcttttca ccaacatatt    60
catagttgaa agttatcctt ctaagtacgt atacaatatt aattaaacgt aaaaacaaaa   120
```

| | |
|---|---|
| ctgactgtaa aaatgtgtaa aaaaaaaata tcaaattcat agcagtttca aggaatgaaa | 180 |
| actattatga tctggtcacg tgtatataaa ttattaattt taaacccata taatttatta | 240 |
| tttttttatt ctaaagttta aagtaattt agtagtattt tatattttga ataaatatac | 300 |
| tttaaatttt tatttttata ttttattact tttaaaaata atgttttat ttaaaacaaa | 360 |
| attataagtt aaaaagttgt tccgaaagta aaatatattt tatagttttt acaaaaataa | 420 |
| attatttta acgtattttt tttaattata ttttgtatg tgattatatc cacaggtatt | 480 |
| atgctgaatt tagctgtttc agtttaccag tgtgatagta tgattttttt tgcctctcaa | 540 |
| aagctatttt tttagaagct tcgtcttaga aataggtggt gtataaattg cggttgactt | 600 |
| ttaactatat atcattttcg atttatttat tacatagaga ggtgcttta atttttaat | 660 |
| tttatttc aataatttta aaagtgggta cttttaaatt ggaacaaagt gaaaatatc | 720 |
| tgttatacgt gcaactgaat tttactgacc ttaaaggact atctcaatcc tggttcagaa | 780 |
| atccttgaaa tgattgatat gttggtggat tttctctgat tttcaaacaa gaggtatttt | 840 |
| atttcatatt tattatattt tttacattta ttttatattt ttttattgtt tggaagggaa | 900 |
| agcgacaatc aaattcaaaa tatattaatt aaactgtaat acttaataag agacaaataa | 960 |
| cagccaagaa tcaaatactg ggttttaat caaagatct ctctacatgc acccaaattc | 1020 |
| attatttaaa tttactatac tacagacaga atatacgaac ccagattaag tagtcagacg | 1080 |
| cttttccgct ttattgagta tatagcctta catattttct gcccataatt tctggattta | 1140 |
| aaataaacaa aaatggttac tttgtagtta tgaaaaaagg cttttccaaa atgcgaaata | 1200 |
| cgtgttattt aaggttaatc aacaaaacgc atatccatat gggtagttgg acaaaacttc | 1260 |
| aatcgat | 1267 |

<210> SEQ ID NO 21
<211> LENGTH: 289
<212> TYPE: DNA
<213> ORGANISM: Artificial Sequence
<220> FEATURE:
<223> OTHER INFORMATION: Synthetic (CYC promoter)

<400> SEQUENCE: 21

| | |
|---|---|
| atttggcgag cgttggttgg tggatcaagc ccacgcgtag gcaatcctcg agcagatccg | 60 |
| ccaggcgtgt atatatagcg tggatggcca ggcaacttta gtgctgacac atacaggcat | 120 |
| atatatgt gtgcgacgac acatgatcat atggcatgca tgtgctctgt atgtatataa | 180 |
| aactcttgtt ttcttctttt ctctaaatat tctttcctta tacattagga cctttgcagc | 240 |
| ataaattact atacttctat agacacgcaa acacaaatac acacactaa | 289 |

<210> SEQ ID NO 22
<211> LENGTH: 401
<212> TYPE: DNA
<213> ORGANISM: Artificial Sequence
<220> FEATURE:
<223> OTHER INFORMATION: Synthetic (TEF promoter)

<400> SEQUENCE: 22

| | |
|---|---|
| atagcttcaa aatgtttcta ctccttttt actcttccag attttctcgg actccgcgca | 60 |
| tcgccgtacc acttcaaaac acccaagcac agcatactaa atttcccctc tttcttcctc | 120 |
| tagggtgtcg ttaattaccc gtactaaagg tttggaaaag aaaaagaga ccgcctcgtt | 180 |
| tcttttctt cgtcgaaaaa ggcaataaaa atttttatca cgtttctttt tcttgaaaat | 240 |
| ttttttttg attttttct ctttcgatga cctcccattg atatttaagt taataaacgg | 300 |

```
tcttcaattt ctcaagtttc agtttcattt ttcttgttct attacaactt ttttttacttc    360 ttgctcatta gaaagaaagc atagcaatct aatctaagtt t                         401

<210> SEQ ID NO 23
<211> LENGTH: 655
<212> TYPE: DNA
<213> ORGANISM: Artificial Sequence
<220> FEATURE:
<223> OTHER INFORMATION: Synthetic (GPD promoter)

<400> SEQUENCE: 23
agtttatcat tatcaatact cgccatttca aagaatacgt aaataattaa tagtagtgat     60
tttcctaact ttatttagtc aaaaaattag ccttttaatt ctgctgtaac ccgtacatgc    120
ccaaaatagg gggcgggtta cacagaatat ataacatcgt aggtgtctgg gtgaacagtt    180
tattcctggc atccactaaa tataatggag cccgcttttt aagctggcat ccagaaaaaa    240
aaagaatccc agcaccaaaa tattgttttc ttcaccaacc atcagttcat aggtccattc    300
tcttagcgca actacagaga acaggggcac aaacaggcaa aaacgggca caacctcaat     360 ggagtgatgc aacctgcctg gagtaaatga tgacacaagg caattgaccc acgcatgtat    420
ctatctcatt ttcttacacc ttctattacc ttctgctctc tctgatttgg aaaaagctga    480
aaaaaaaggt tgaaaccagt tccctgaaat tattccccta cttgactaat aagtatataa    540
agacggtagg tattgattgt aattctgtaa atctatttct taaacttctt aaattctact    600
tttatagtta gtcttttttt tagttttaaa acaccagaac ttagtttcga cggat         655

<210> SEQ ID NO 24
<211> LENGTH: 1468
<212> TYPE: DNA
<213> ORGANISM: Artificial Sequence
<220> FEATURE:
<223> OTHER INFORMATION: Synthetic (ADH promoter)

<400> SEQUENCE: 24
gccgggatcg aagaaatgat ggtaaatgaa ataggaaatc aaggagcatg aaggcaaaag     60
acaaatataa gggtcgaacg aaaaataaag tgaaagtgt tgatatgatg tatttggctt    120
tgcggcgccg aaaaaacgag tttacgcaat tgcacaatca tgctgactct gtggcggacc    180
cgcgctcttg ccggcccggc gataacgctg gcgtgaggc tgtgcccggc ggagtttttt    240
gcgcctgcat tttccaaggt ttaccctgcg ctaaggggcg agattggaga agcaataaga    300
atgccggttg gggttgcgat gatgacgacc acgacaactg tgtcattat ttaagttgcc    360 gaaagaacct gagtgcattt gcaacatgag tatactagaa gaatgagcca agacttgcga    420
gacgcgagtt tgccggtggt gcgaacaata gagcgaccat gaccttgaag gtgagacgcg    480
cataaccgct agagtacttt gaagaggaaa cagcaatagg gttgctacca gtataaatag    540
acaggtacat acaacactgg aaatggttgt ctgtttgagt acgctttcaa ttcatttggg    600
tgtgcacttt attatgttac aatatggaag ggaactttac acttctccta tgcacatata    660
ttaattaaag tccaatgcta gtagagaagg ggggtaacac ccctccgcgc tcttttccga    720 ttttttttcta aaccgtggaa tatttcggat atccttttgt tgtttccggg tgtacaatat    780
ggacttcctc ttttctggca accaaaccca tacatcggga ttcctataat accttcgttg    840
gtctccctaa catgtaggtg gcggagggga gatatacaat agaacagata ccagacaaga    900
cataatgggc taaacaagac tacaccaatt acactgcctc attgatggtg gtacataacg    960
```

```
aactaatact gtagccctag acttgatagc catcatcata tcgaagtttc actacccttt      1020
ttccatttgc catctattga agtaataata ggcgcatgca acttcttttc ttttttttc      1080 ttttctctct cccccgttgt tgtctcacca tatccgcaat gacaaaaaaa tgatggaaga      1140
cactaaagga aaaaattaac gacaaagaca gcaccaacag atgtcgttgt tccagagctg      1200
atgaggggta tctcgaagca cacgaaactt tttccttcct tcattcacgc acactactct      1260
ctaatgagca acggtatacg gccttccttc cagttacttg aatttgaaat aaaaaaaagt      1320
ttgctgtctt gctatcaagt ataaatagac ctgcaattat taatctttg tttcctcgtc       1380 attgttctcg ttcctttct tccttgtttc tttttctgca caatatttca agctatacca       1440
agcatacaat caactccaag ctggccgc                                         1468

<210> SEQ ID NO 25
<211> LENGTH: 252
<212> TYPE: DNA
<213> ORGANISM: Artificial Sequence
<220> FEATURE:
<223> OTHER INFORMATION: Synthetic (CYC1 terminator)

<400> SEQUENCE: 25
tcatgtaatt agttatgtca cgcttacatt cacgccctcc ccccacatcc gctctaaccg       60
aaaaggaagg agttagacaa cctgaagtct aggtccctat ttattttttt atagttatgt      120
tagtattaag aacgttattt atatttcaaa tttttctttt ttttctgtac agacgcgtgt      180
acgcatgtaa cattatactg aaaaccttgc ttgagaaggt tttgggacgc tcgaaggctt      240
taatttgcgg cc                                                          252

<210> SEQ ID NO 26
<211> LENGTH: 31
<212> TYPE: DNA
<213> ORGANISM: Artificial Sequence
<220> FEATURE:
<223> OTHER INFORMATION: Synthetic (forward primer)

<400> SEQUENCE: 26
cgagctcttc gcggccacct acgccgctat c                                      31

<210> SEQ ID NO 27
<211> LENGTH: 32
<212> TYPE: DNA
<213> ORGANISM: Artificial Sequence
<220> FEATURE:
<223> OTHER INFORMATION: Synthetic (reverse primer)

<400> SEQUENCE: 27
gctctagata ttgatatagt gtttaagcga at                                     32

<210> SEQ ID NO 28
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 28
ggatccatgt ccgtaaagga actact                                            26

<210> SEQ ID NO 29
<211> LENGTH: 34
<212> TYPE: DNA
<213> ORGANISM: Artificial Sequence
```

```
<220> FEATURE:
<223> OTHER INFORMATION: Synthetic (reverse primer)

<400> SEQUENCE: 29
acgcgtcgac ttaaaactgc aattcctttt gaat                           34

<210> SEQ ID NO 30
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 30
gagctcaatt aaccctcact aaaggg                                    26

<210> SEQ ID NO 31
<211> LENGTH: 26
<212> TYPE: DNA
<213> ORGANISM: Artificial Sequence
<220> FEATURE:
<223> OTHER INFORMATION: Synthetic (reverse primer)

<400> SEQUENCE: 31
gagctccaaa ttaaagcctt cgagcg                                    26

<210> SEQ ID NO 32
<211> LENGTH: 60
<212> TYPE: DNA
<213> ORGANISM: Artificial Sequence
<220> FEATURE:
<223> OTHER INFORMATION: Synthetic (forward primer)

<400> SEQUENCE: 32
aagatctacg aagttgaagg tatgagatgg gctggtaacg ccagtcacga cgttgtaaaa    60

<210> SEQ ID NO 33
<211> LENGTH: 60
<212> TYPE: DNA
<213> ORGANISM: Artificial Sequence
<220> FEATURE:
<223> OTHER INFORMATION: Synthetic (reverse primer)

<400> SEQUENCE: 33
gcttccttaa cttctggctt ggacaaggta ccgacgtaaa aggtttcccg actggaaagc    60

<210> SEQ ID NO 34
<211> LENGTH: 70
<212> TYPE: DNA
<213> ORGANISM: Artificial Sequence
<220> FEATURE:
<223> OTHER INFORMATION: Synthetic (forward primer)

<400> SEQUENCE: 34
cgatgcgtat tttaagtggt tctctgaaca gcacaatgtc ctcgacacca ccagtcacga    60
cgttgtaaaa                                                          70

<210> SEQ ID NO 35
<211> LENGTH: 72
<212> TYPE: DNA
<213> ORGANISM: Artificial Sequence
<220> FEATURE:
<223> OTHER INFORMATION: Synthetic (reverse primer)

<400> SEQUENCE: 35
```

```
ggatcacccc ccactcaagt cgttgcattg ctaacatgtg gcattctgcc caaggtttcc      60
cgactggaaa gc                                                         72
```

<210> SEQ ID NO 36
<211> LENGTH: 70
<212> TYPE: DNA
<213> ORGANISM: Artificial Sequence
<220> FEATURE:
<223> OTHER INFORMATION: Synthetic (forward primer)

<400> SEQUENCE: 36

```
ccctatgtct ctggccgatc acgcgccatt gtccctcaga aacaaatcaa ccagtcacga      60
cgttgtaaaa                                                            70
```

<210> SEQ ID NO 37
<211> LENGTH: 70
<212> TYPE: DNA
<213> ORGANISM: Artificial Sequence
<220> FEATURE:
<223> OTHER INFORMATION: Synthetic (reverse primer)

<400> SEQUENCE: 37

```
tagaagcaac tgtgccgaca gcctctgaat gagtggtgtt gtaaccaccc aggtttcccg      60
actggaaagc                                                            70
```

<210> SEQ ID NO 38
<211> LENGTH: 22
<212> TYPE: DNA
<213> ORGANISM: Artificial Sequence
<220> FEATURE:
<223> OTHER INFORMATION: Synthetic (forward primer)

<400> SEQUENCE: 38

```
gctcttctct accctgtcat tc                                              22
```

<210> SEQ ID NO 39
<211> LENGTH: 22
<212> TYPE: DNA
<213> ORGANISM: Artificial Sequence
<220> FEATURE:
<223> OTHER INFORMATION: Synthetic (reverse primer)

<400> SEQUENCE: 39

```
tagtgtacag ggtgtcgtat ct                                              22
```

<210> SEQ ID NO 40
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 40

```
ggagttgaag gcaaaattag aagtga                                          26
```

<210> SEQ ID NO 41
<211> LENGTH: 26
<212> TYPE: DNA
<213> ORGANISM: Artificial Sequence
<220> FEATURE:
<223> OTHER INFORMATION: Synthetic (reverse primer)

<400> SEQUENCE: 41

```
attcccttc ctgcacaaca cgagat                                           26
```

<210> SEQ ID NO 42
<211> LENGTH: 25
<212> TYPE: DNA
<213> ORGANISM: Artificial Sequence
<220> FEATURE:
<223> OTHER INFORMATION: Synthetic (forward primer)

<400> SEQUENCE: 42
tcaatgagac tgttgtcctc ctact                                          25

<210> SEQ ID NO 43
<211> LENGTH: 24
<212> TYPE: DNA
<213> ORGANISM: Artificial Sequence
<220> FEATURE:
<223> OTHER INFORMATION: Synthetic (reverse primer)

<400> SEQUENCE: 43
tacatccttg tcgagccttg ggca                                           24

<210> SEQ ID NO 44
<211> LENGTH: 69
<212> TYPE: DNA
<213> ORGANISM: Artificial Sequence
<220> FEATURE:
<223> OTHER INFORMATION: Synthetic (forward primer)

<400> SEQUENCE: 44
tgagcacgtg agtatacgtg attaagcaca caaaggcagc ttggagtatg gtgctgcaag    60
gcgattaag                                                            69

<210> SEQ ID NO 45
<211> LENGTH: 67
<212> TYPE: DNA
<213> ORGANISM: Artificial Sequence
<220> FEATURE:
<223> OTHER INFORMATION: Synthetic (reverse primer)

<400> SEQUENCE: 45
aggcaagtgc acaaacaata cttaaataaa tactactcag taataacccg gctcgtatgt    60
tgtgtgg                                                              67

<210> SEQ ID NO 46
<211> LENGTH: 21
<212> TYPE: DNA
<213> ORGANISM: Artificial Sequence
<220> FEATURE:
<223> OTHER INFORMATION: Synthetic (forward primer)

<400> SEQUENCE: 46
gccaaatgat ttagcattat c                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetic (reverse primer)

<400> SEQUENCE: 47
aaaaggagag ggccaagagg g                                              21

<210> SEQ ID NO 48

<211> LENGTH: 60
<212> TYPE: DNA
<213> ORGANISM: Artificial Sequence
<220> FEATURE:
<223> OTHER INFORMATION: Synthetic (forward primer)

<400> SEQUENCE: 48
atgattagac aatcattaat gaaaacagtg tgggctaact ccagtcacga cgttgtaaaa    60

<210> SEQ ID NO 49
<211> LENGTH: 60
<212> TYPE: DNA
<213> ORGANISM: Artificial Sequence
<220> FEATURE:
<223> OTHER INFORMATION: Synthetic (reverse primer)

<400> SEQUENCE: 49
ctagatagat gaatctctac ccaagaaata aactttagcc aggtttcccg actggaaagc    60

<210> SEQ ID NO 50
<211> LENGTH: 22
<212> TYPE: DNA
<213> ORGANISM: Artificial Sequence
<220> FEATURE:
<223> OTHER INFORMATION: Synthetic (forward primer)

<400> SEQUENCE: 50
actgatcatc atttaaaaat gt                                             22

<210> SEQ ID NO 51
<211> LENGTH: 22
<212> TYPE: DNA
<213> ORGANISM: Artificial Sequence
<220> FEATURE:
<223> OTHER INFORMATION: Synthetic (reverse primer)

<400> SEQUENCE: 51
aaggaaaaaa attttcacac ta                                             22

<210> SEQ ID NO 52
<211> LENGTH: 112
<212> TYPE: DNA
<213> ORGANISM: Saccharomyces cerevisiae

<400> SEQUENCE: 52
tagaatggat atccttgaaa atatatatat attgctgaaa tgtaaaaggt aagaaaagtt    60
agaaagtaag acgattgcta accacctatt ggaaaaaaca ataggtcctt aa           112

<210> SEQ ID NO 53
<211> LENGTH: 36
<212> TYPE: DNA
<213> ORGANISM: Artificial Sequence
<220> FEATURE:
<223> OTHER INFORMATION: Synthetic (forward primer)

<400> SEQUENCE: 53
cggaattcta gaatggtata tccttgaaat atatat                              36

<210> SEQ ID NO 54
<211> LENGTH: 34
<212> TYPE: DNA
<213> ORGANISM: Artificial Sequence
<220> FEATURE:
<223> OTHER INFORMATION: Synthetic (reverse primer)

<400> SEQUENCE: 54

```
cggaattcca atattattta aggacctatt gttt                                34
```

<210> SEQ ID NO 55
<211> LENGTH: 296
<212> TYPE: DNA
<213> ORGANISM: Saccharomyces cerevisiae

<400> SEQUENCE: 55

```
tttggcgagc gttggttggt ggatcaagcc cacgcgtagg caatcctcga gcagatccgc    60
caggcgtgta tatatagcgt ggatggccag gcaactttag tgctgacaca tacaggcata  120
tatatatgtg tgcgacgaca catgatcata tggcatgcat gtgctctgta tgtatataaa  180
actcttgttt tcttcttttc tctaaatatt ctttccttat acattaggac ctttgcagca  240
taaattacta tacttctata gacacacaaa cacaaataca cacactaaat taataa      296
```

<210> SEQ ID NO 56
<211> LENGTH: 27
<212> TYPE: DNA
<213> ORGANISM: Artificial Sequence
<220> FEATURE:
<223> OTHER INFORMATION: Synthetic (forward primer)

<400> SEQUENCE: 56

```
cggaattcat ttggcgagcg ttggttg                                        27
```

<210> SEQ ID NO 57
<211> LENGTH: 31
<212> TYPE: DNA
<213> ORGANISM: Artificial Sequence
<220> FEATURE:
<223> OTHER INFORMATION: Synthetic (reverse primer)

<400> SEQUENCE: 57

```
cggaattctt agtgtgtgta tttgtgtttg c                                   31
```

<210> SEQ ID NO 58
<211> LENGTH: 41
<212> TYPE: DNA
<213> ORGANISM: Artificial Sequence
<220> FEATURE:
<223> OTHER INFORMATION: Synthetic (forward primer)

<400> SEQUENCE: 58

```
gtcgagtcga ctctagagga tcctagaatg gtatatcctt g                        41
```

<210> SEQ ID NO 59
<211> LENGTH: 39
<212> TYPE: DNA
<213> ORGANISM: Artificial Sequence
<220> FEATURE:
<223> OTHER INFORMATION: Synthetic (reverse primer)

<400> SEQUENCE: 59

```
gagctcggta cccggggatc cttaaggacc tattgtttt                           39
```

<210> SEQ ID NO 60
<211> LENGTH: 41
<212> TYPE: DNA
<213> ORGANISM: Artificial Sequence
<220> FEATURE:
<223> OTHER INFORMATION: Synthetic (forward primer)

<400> SEQUENCE: 60

```
gtcgagtcga ctctagagga tcctttggcg agcgttggtt g                   41
```

<210> SEQ ID NO 61
<211> LENGTH: 39
<212> TYPE: DNA
<213> ORGANISM: Artificial Sequence
<220> FEATURE:
<223> OTHER INFORMATION: Synthetic (reverse primer)

<400> SEQUENCE: 61

```
gagctcggta cccggggatc cattaattta gtgtgtgta                      39
```

<210> SEQ ID NO 62
<211> LENGTH: 64
<212> TYPE: DNA
<213> ORGANISM: Artificial Sequence
<220> FEATURE:
<223> OTHER INFORMATION: Synthetic (forward primer)

<400> SEQUENCE: 62

```
atgagcagta gcaagaaatt ggccggtctt agggacaatt tcctattacg ccagctggcg   60
aaag                                                            64
```

<210> SEQ ID NO 63
<211> LENGTH: 60
<212> TYPE: DNA
<213> ORGANISM: Artificial Sequence
<220> FEATURE:
<223> OTHER INFORMATION: Synthetic (reverse primer)

<400> SEQUENCE: 63

```
ttacttttt tgggatgggg gtagggtttc ttcttctagg ggctttacac tttatgcttc    60
```

<210> SEQ ID NO 64
<211> LENGTH: 21
<212> TYPE: DNA
<213> ORGANISM: Artificial Sequence
<220> FEATURE:
<223> OTHER INFORMATION: Synthetic (forward primer)

<400> SEQUENCE: 64

```
caatcatgtc ctcgacctta a                                         21
```

<210> SEQ ID NO 65
<211> LENGTH: 19
<212> TYPE: DNA
<213> ORGANISM: Artificial Sequence
<220> FEATURE:
<223> OTHER INFORMATION: Synthetic (reverse primer)

<400> SEQUENCE: 65

```
gaagatgttt cgctaaaag                                            19
```

<210> SEQ ID NO 66
<211> LENGTH: 20
<212> TYPE: DNA
<213> ORGANISM: Artificial Sequence
<220> FEATURE:
<223> OTHER INFORMATION: Synthetic (forward primer)

<400> SEQUENCE: 66

```
cttactttcg gtatccttac                                           20
```

<210> SEQ ID NO 67
<211> LENGTH: 20

```
<212> TYPE: DNA
<213> ORGANISM: Artificial Sequence
<220> FEATURE:
<223> OTHER INFORMATION: Synthetic (reverse primer)

<400> SEQUENCE: 67
catggtaagt gaaagcatta                                           20

<210> SEQ ID NO 68
<211> LENGTH: 60
<212> TYPE: DNA
<213> ORGANISM: Artificial Sequence
<220> FEATURE:
<223> OTHER INFORMATION: Synthetic (forward primer)

<400> SEQUENCE: 68
cgtcacgtgt tttgccattt tgtacgacaa atgaaccgcc tcaaccctat ctcggtctat   60

<210> SEQ ID NO 69
<211> LENGTH: 66
<212> TYPE: DNA
<213> ORGANISM: Artificial Sequence
<220> FEATURE:
<223> OTHER INFORMATION: Synthetic (reverse primer)

<400> SEQUENCE: 69
tgaagttatc tctcaagccg gcgaattttc tttgcgacat gaattcttat taatttagtg   60
tgtgta                                                          66

<210> SEQ ID NO 70
<211> LENGTH: 73
<212> TYPE: DNA
<213> ORGANISM: Artificial Sequence
<220> FEATURE:
<223> OTHER INFORMATION: Synthetic (reverse primer)

<400> SEQUENCE: 70
tgaagttatc tctcaagccg gcgaattttc tttgcgacat gaattccaat attatatcct   60
taaggaccta ttg                                                  73

<210> SEQ ID NO 71
<211> LENGTH: 62
<212> TYPE: DNA
<213> ORGANISM: Artificial Sequence
<220> FEATURE:
<223> OTHER INFORMATION: Synthetic (forward primer)

<400> SEQUENCE: 71
tggaatggtc taagaagaaa acctacagtc gatcaaaaat cctcgaggag aacttctagt   60
at                                                              62

<210> SEQ ID NO 72
<211> LENGTH: 73
<212> TYPE: DNA
<213> ORGANISM: Artificial Sequence
<220> FEATURE:
<223> OTHER INFORMATION: Synthetic (reverse primer)

<400> SEQUENCE: 72
gatttgttgg ttgtcctaga agaagaaacc ctaccccat gaattccaat attatatcct    60
taaggaccta ttg                                                  73

<210> SEQ ID NO 73
```

```
<211> LENGTH: 292
<212> TYPE: DNA
<213> ORGANISM: Artificial Sequence
<220> FEATURE:
<223> OTHER INFORMATION: Synthetic (ccw12 promoter)

<400> SEQUENCE: 73
ttcgcggcca cctacgccgc tatctttgca acaactatct gcgataactc agcaaatttt      60
gcatattcgt gttgcagtat tgcgataatg ggagtcttac ttccaacata acggcagaaa     120
gaaatgtgag aaaattttgc atcctttgcc tccgttcaag tatataaagt cggcatgctt     180
gataatcttt ctttccatcc tacattgttc taattattct tattctcctt tattctttcc     240
taacatacca agaaattaat cttctgtcat tcgcttaaac actatatcaa ta             292
```